(12) United States Patent
Matsusita et al.

(10) Patent No.: US 7,383,156 B2
(45) Date of Patent: Jun. 3, 2008

(54) APPARATUS FOR INSPECTING WAFER SURFACE, METHOD FOR INSPECTING WAFER SURFACE, APPARATUS FOR JUDGING DEFECTIVE WAFER, METHOD FOR JUDGING DEFECTIVE WAFER, AND APPARATUS FOR PROCESSING INFORMATION ON WAFER SURFACE

(75) Inventors: Kouzou Matsusita, Miyazaki (JP); Yukinori Matsumura, Isehara (JP); Tomikazu Tanuki, Fujisawa (JP); Mitsuo Terada, Miyazaki (JP); Kotaro Hori, Hiratsuka (JP); Kiyoharu Miyakawa, Kiyotake (JP); Akira Nisi, Kiyotake (JP); Hirobumi Miwa, Hiratsuka (JP)

(73) Assignee: Sumco Techxiv Kabushiki Kaisha, Nagasaki (JP)

( * ) Notice: Subject to any disclaimer, the term of this patent is extended or adjusted under 35 U.S.C. 154(b) by 525 days.

(21) Appl. No.: 10/363,746

(22) PCT Filed: Sep. 5, 2001

(86) PCT No.: PCT/JP01/07699

§ 371 (c)(1),
(2), (4) Date: Aug. 25, 2003

(87) PCT Pub. No.: WO02/21111

PCT Pub. Date: Mar. 14, 2002

(65) Prior Publication Data

US 2004/0036863 A1 Feb. 26, 2004

(30) Foreign Application Priority Data

| Sep. 5, 2000 | (JP) | 2000-269147 |
| Sep. 5, 2000 | (JP) | 2000-269163 |
| Sep. 29, 2000 | (JP) | 2000-301146 |
| Sep. 29, 2000 | (JP) | 2000-301148 |

(51) Int. Cl.
*G06F 19/00* (2006.01)
*G06F 17/40* (2006.01)

(52) U.S. Cl. .............. 702/183; 356/237.1; 356/237.2; 356/237.3; 356/237.4; 356/237.5; 382/100; 382/108; 382/145; 382/149; 382/190; 382/194; 700/90; 700/108; 700/109; 700/110; 702/33; 702/35; 702/182; 702/187

(58) Field of Classification Search ............... 340/679, 340/680; 356/388, 390, 237.1, 237.2, 237.3, 356/237.4, 237.5; 382/100, 108, 142, 145, 382/146, 147, 148, 149, 150, 151, 152, 190, 382/192, 194, 195; 700/90, 108, 109, 110; 702/33, 35, 40, 182, 283, 185, 187, 188, 702/183

See application file for complete search history.

(56) References Cited

U.S. PATENT DOCUMENTS 4,532,650 A * 7/1985 Wihl et al. .................. 382/144

(Continued)

FOREIGN PATENT DOCUMENTS

EP 0 910 123 4/1999

(Continued)

*Primary Examiner*—Edward R Cosimano
(74) *Attorney, Agent, or Firm*—Welsh & Katzm, Ltd.

(57) ABSTRACT

It is possible to inspect scratches and staining on a wafer surface on the basis of an LPD map obtained from a particle counter 11, by providing a means 21 for detecting aggregation of clustered point defects (LPD) from two-dimensional distribution information 30 for such fine LPD on the surface of a silicon wafer, and an improvement in the inspection efficiency and the precision of judgements of "defective" status can be achieved. Furthermore, the system is devised so that the trend of generation of scratches and staining in a specified process can easily be detected by accumulating wafer surface information such as scratch information, staining information and the like for the wafer surface detected by a wafer surface inspection device 11 (especially as image information or numerical information), and superposing sets of information thus accumulated. Plans for improving processes can be made by both the wafer supplier and wafer consumer by sharing such information with both parties.

20 Claims, 22 Drawing Sheets

U.S. PATENT DOCUMENTS

| | | | |
|---|---|---|---|
| 4,589,139 A * | 5/1986 | Hada et al. | 382/144 |
| 5,479,252 A | 12/1995 | Worster et al. | |
| 5,619,588 A * | 4/1997 | Yolles et al. | 382/149 |
| 5,761,064 A | 6/1998 | La et al. | |
| 5,828,778 A | 10/1998 | Hagi et al. | |
| 5,900,941 A * | 5/1999 | Matsuyama et al. | 356/394 |
| 5,907,628 A * | 5/1999 | Yolles et al. | 382/149 |
| 5,913,105 A | 6/1999 | McIntyre et al. | |
| 6,611,728 B1 * | 8/2003 | Morioka et al. | 700/109 |
| 6,876,445 B2 * | 4/2005 | Shibuya et al. | 356/237.2 |
| 7,061,602 B2 * | 6/2006 | Hamamatsu et al. | 356/237.2 |
| 2005/0196033 A1 * | 9/2005 | Hamamatsu et al. | 382/149 |

FOREIGN PATENT DOCUMENTS

| | | | |
|---|---|---|---|
| JP | 03-209740 A | * | 9/1991 |
| JP | 09-199551 A | * | 7/1997 |
| JP | 10-221040 A | * | 8/1998 |
| JP | 11-110561 A | * | 4/1999 |
| JP | 2000-77495 A | * | 3/2000 |
| WO | WO 00/14790 A1 | * | 3/2000 |

* cited by examiner (a : 200×200 Dots)

(b : 400×400 Dots)

(c : 1000×1000 Dots)

[DEGREE OF SIMILARITY OF ANGLE] = | COS ($\theta_1-\theta_2$) || COS ($\theta_2-\theta_3$) || COS ($\theta_3-\theta_1$) |

FIG.15(A)

| | DETECTION METHOD |
|---|---|
| SCRATCH | TWO-DIMENSIONAL HALF CONVERSION |
| SCRATCH | SPACE FILTER |

FIG.15(B)

| | JUDGMENT |
|---|---|
| SCRATCH | SECOND SCRATCH NG LONG SCRATCH NG |
| STAINING | DARK AND LARGE STAINING NG |

⇩

| | LARGE | SMALL |
|---|---|---|
| DARK | × | △ |
| LIGHT | △ | ○ |

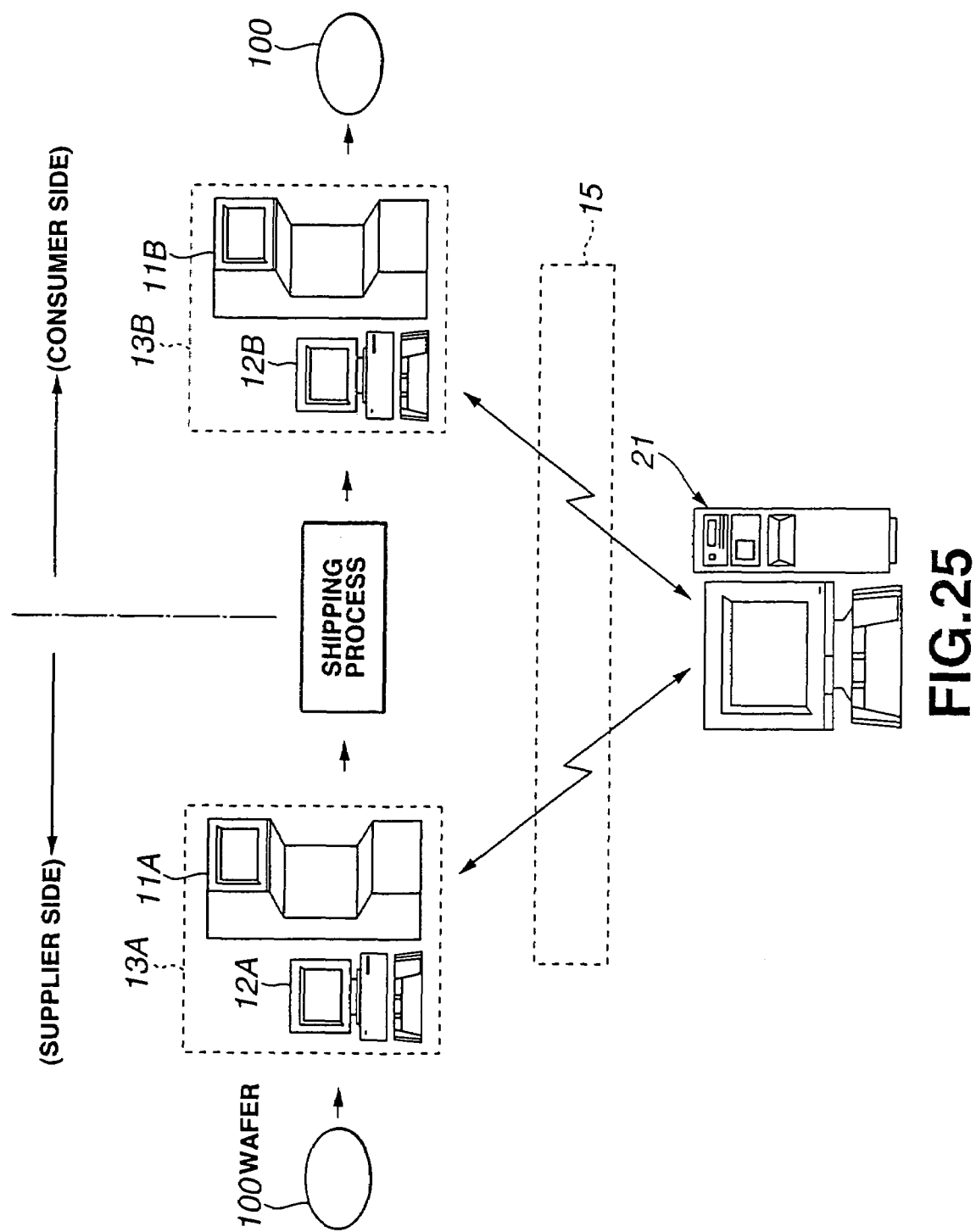

APPARATUS FOR INSPECTING WAFER SURFACE, METHOD FOR INSPECTING WAFER SURFACE, APPARATUS FOR JUDGING DEFECTIVE WAFER, METHOD FOR JUDGING DEFECTIVE WAFER, AND APPARATUS FOR PROCESSING INFORMATION ON WAFER SURFACE

TECHNICAL FIELD

The present invention relates to a wafer surface inspection device and method which makes it possible to extract and classify defects such as scratches, staining and the like in a device that inspects the surfaces of silicon wafers for the presence or absence of scratches and staining. Furthermore, the present invention also relates to a judgement device and method which make it possible to perform judgements in accordance with the types of defects such as scratches, staining and the like in a device that judges defective wafers on the basis of scratches and staining on the surfaces of silicon wafers. Moreover, the present invention relates to a wafer surface information processing device which is used to accumulate wafer surface scratch information and staining information detected by the wafer surface inspection device, and to provide such information for use in wafer processing processes and other processes.

BACKGROUND ART

In silicon wafer manufacturing processes, the surfaces of silicon wafers that have been cut from a silicon ingot drawn up by the CZ (Czokralski) method or the like are finished to a mirror surface state by a lapping treatment using a polishing liquid containing a polishing agent that has a fine particle size.

Then, after passing through a cleaning process, the surfaces of the silicon wafers that have been subjected to such a surface finishing treatment are inspected visually by a worker, and only wafers in which no scratches or staining are observed are shipped as satisfactory wafers.

In the case of visual inspection of the wafer surfaces by a human being, the methods and judgement criteria used have not been standardized, so that such procedures are inadequate in terms of enhancing the degree of customer satisfaction.

The present invention was devised in light of such problems; a first object of the present invention is to provide a wafer surface inspection device and method which allow the reliable detection of scratches and staining that are cause for a judgement of "defective".

Furthermore, a second object of the present invention is to provide a defective wafer judgment device and method which allow the reliable detection of scratches and staining that are cause for a judgement of "defective" in accordance with characteristic quantities relating to these scratches and staining.

Furthermore, a third object of the present invention is to provide a wafer surface information processing device which accumulates wafer surface information and provides this information for use in wafer treatment processes and other processes.

It is convenient to be able to grasp the types of scratches and haze occurring on the surfaces of wafers in various processes such as wafer treatment processes, conveying processes and the like. This makes it possible to make accurate modifications in various, and is also useful in the planning of modifications and the like.

Furthermore, if mutual understanding of intentions between the wafer supplier (wafer maker) and user is facilitated, the wafer supplier can supply wafers with a quality that accurately meets the requirements of the user, and the user can easily communicate his own requirements to the wafer supplier.

The present invention was devised in light of the abovementioned problems; a fourth object of the present invention is to provide a system which is devised so that trends in the occurrence of scratches and haze in specified processes can easily be detected, and information concerning these trends can be freely exchanged between wafer suppliers and consumers.

DISCLOSURE OF THE INVENTION

In order to achieve the abovementioned first object, the wafer surface inspection device of the present invention is a device which detects aggregation of clustered fine point defects (LPD) from distribution information concerning such LPD on the surface of a silicon wafer, and which comprises means for accurately detecting defects that are cause for a judgement of "defective".

In more concrete terms, the present invention provides the following wafer surface inspection device and wafer surface inspection method.

(1) A wafer surface inspection device which detects scratches on a wafer surface on the basis of two-dimensional defect distribution information (i.e., an LPD map) for the wafer surface supplied from a particle counter, comprising input means for inputting the abovementioned LPD map supplied from the abovementioned particle counter, memory means capable of accumulating the abovementioned LPD map for each of a plurality of wafers, and information processing means for detecting scratches on the wafer surface by detecting the cluster of LPD in the LPD maps accumulated in the abovementioned memory means.

The term "particle counter" refers to a device that detects scattered light that is obtained from the wafer surface when the wafer surface is illuminated with laser light. A commercially marketed particle counter may be used. The main function of this inspection device is to judge the status of respective scattering points (LPD: light point defects) as defects. The recognition of such LPD as linear scratches or staining from the two-dimensional state of aggregation of these LPD, and the performance of an inspection similar to an inspection performed by a human being in order to determine whether or not such scratches and staining are cause for a judgement of "defective", have proved to be difficult. Accordingly, it is necessary for a worker to examine this map in order to detect scratches and judge the relative status of these scratches as defects; the technology has been inadequate in terms of realizing a procedure for performing inspections that does not require human intervention. Specifically, in the case of current inspection devices, scratches and staining consisting of aggregation of LPD cannot be automatically recognized as such from LPD maps. However, this is made possible by installing the inspection device of the present invention.

"Aggregation of LPD (scratches) on the wafer surface" may be either continuous or discontinuous. Furthermore, the arrangement of such aggregation may be either rectilinear or curvilinear. The term "scratches" refers to scratches of various configurations, such as aggregation of defects on the wafer surface, rubbing scratches on the wafer surface and the like. Furthermore, the term "memory means capable of accumulating for a plurality of wafers" refers to means that can accumulate for a plurality of wafers or for a single wafer.

(2) The wafer surface inspection device according to (1), characterized in that the abovementioned information processing means detect the abovementioned scratches by two-dimensional half-conversion processing for each of the abovementioned partial area LPD maps.

(3) The wafer surface inspection device according to (1), characterized in that the abovementioned information processing means detect the abovementioned LPD aggregation in distinction from the surrounding areas by smoothing the abovementioned LPD map by means of a space filter, and binarizing the result with a specified threshold value.

(4) A wafer surface inspection method in which scratches on a wafer surface are detected on the basis of two-dimensional defect distribution information (i.e., an LPD map) for the wafer surface supplied from a particle counter, characterized in that this method comprises a step in which defects consisting of aggregation of LPD on the wafer surface are detected by detecting the cluster of LPD in the LPD map extracted from the wafer surface.

(5) The wafer surface inspection method according to (4), characterized in that the abovementioned defects (scratch defects) are detected by detecting aggregation of linearly clustered LPD by means of two-dimensional half-conversion processing for each partial area of the abovementioned LPD map in the step in which the abovementioned defects are detected.

(6) The wafer surface inspection method according to (4), characterized in that this method further comprises a step in which indefinite-form aggregation of the abovementioned LPD are detected as defects (staining defects) in distinction from the surrounding areas by smoothing at least a portion of the abovementioned LPD map by means of a space filter, and binarizing the result with a specified threshold value.

(7) A computer-readable memory medium which accommodates a program that includes a detection step in which defects comprising aggregation of LPD on a wafer surface are detected by detecting the cluster of LPD in an LPD map on the basis of two-dimensional defect distribution information (i.e., the abovementioned LPD map) extracted from the wafer surface.

In order to achieve the abovementioned second object, the judgement device of the present invention is characterized in that the device comprises means for detecting the types of scratches and staining extracted on the basis of distribution information for fine point defects (LPD) on the surface of the silicon wafer from characterizing quantities relating to such scratches and staining, and judging defective wafers on the basis of criteria corresponding to these characterizing quantities.

In more concrete terms, the present invention provides the following judgement device and judgement method.

(8) A judgement device which judges whether or not wafers that have scratches and staining on the surface are acceptable as products on the basis of information concerning scratches and staining supplied from a wafer surface inspection device that detects scratches and staining on the wafer surface on the basis of an LPD map, comprising input means for inputting the abovementioned information concerning scratches and staining on the wafer that is supplied from the abovementioned wafer surface inspection device, memory means capable of accumulating the abovementioned information concerning scratches and staining for each of a plurality of wafers, and information processing means for detecting the type and degree of the abovementioned scratches from characteristic quantities relating to the abovementioned scratches in the abovementioned information stored in the abovementioned memory means, detecting the degree of the abovementioned staining from characteristic quantities relating to this staining in the abovementioned information stored in the abovementioned memory means, and performing the abovementioned judgement on the basis of criteria corresponding to the type and degree of the abovementioned detected scratches and/or on the basis of criteria corresponding to the degree of the abovementioned detected staining.

The term "wafer surface inspection device" refers to a device that detects scattered light that is obtained from the wafer surface when the wafer surface is illuminated with laser light. A commercially device may be used. The main function of this inspection device is to judge the status of respective scattering points (LPD: point defects) as defects. The recognition of such LPD as linear scratches or staining from the two-dimensional state of aggregation of these LPD, and the performance of an inspection similar to an inspection performed by a human being in order to determine whether or not such scratches and staining are cause for a judgement of "defective", have proved to be difficult. Accordingly, it is necessary for a worker to examine this map in order to detect scratches and judge the relative status of these scratches as defects; the technology has been inadequate in terms of realizing a procedure for performing inspections that does not require human intervention. Specifically, in the case of current inspection devices, scratches and staining consisting of aggregation of LPD cannot be automatically recognized as such from LPD maps. However, this is made possible by installing the inspection device of the present invention.

"Aggregation of LPD (scratches) on the wafer surface" may be either continuous or discontinuous. Furthermore, the arrangement of such aggregation may be either rectilinear or curvilinear. The term "scratches" refers to scratches of various configurations, such as aggregation of defects on the wafer surface, rubbing scratches on the wafer surface and the like. Furthermore, the term "type" has a qualitative meaning, and the term "degree" has a quantitative meaning. Moreover, the term "information concerning scratches and staining that is supplied from the wafer surface inspection device" includes visual screen information and numerical information.

The term "memory means capable of accumulating for a plurality of wafers" refers to means that can accumulate for a plurality of wafers or for a single wafer.

(9) The judgement device according to (8), characterized in that the abovementioned characteristic quantities relating to the abovementioned scratches or staining are a depth and size of the abovementioned scratches or staining.

(10) The judgement device according to (8), characterized in that the abovementioned characteristic quantities relating to the abovementioned scratches constitute one or more items selected from a group consisting of the length, density, width, linearity, curvature and position of the abovementioned scratches.

(11) The judgement device according to (8), characterized in that the abovementioned characteristic quantities relating to the abovementioned staining constitute one or more items selected from a group consisting of the area, depth/density, distribution, shape and position of the abovementioned staining.

(12) A judgement method for judging whether or not wafers that have scratches and staining on the surface are acceptable as products on the basis of information concerning scratches and staining supplied from a wafer surface inspection device that detects the scratches and staining on the wafer surface on the basis of an LPD map, comprising the steps of detecting the type and degree of the abovementioned scratches from characteristic quantities relating to scratches in the abovementioned information, and detecting the degree of the abovementioned staining from characteristic quantities relating to staining in the abovementioned information, and performing the abovementioned judgement on the basis of criteria corresponding to the type and degree of the abovementioned detected scratches and/or on the basis of criteria corresponding to the degree of the abovementioned detected staining.

(13) The judgement method according to (12), characterized in that the characteristic quantities relating to the abovementioned scratches or staining are the depth and size of the abovementioned scratches or staining.

(14) A computer-readable memory medium which accommodates a program that includes a judgement step in which the type and degree of scratches are detected on the basis of characteristic quantities relating to the abovementioned scratches in wafer surface information (information concerning scratches and staining on the wafer surface) that is supplied from a wafer surface inspection device, the degree of staining is detected on the basis of characteristic quantities relating to the abovementioned staining in the abovementioned surface information, and a judgement is made as to whether or not the abovementioned wafer is acceptable as a product on the basis of criteria corresponding to the type and degree of the abovementioned scratches and/or on the basis of criteria corresponding to the degree of the abovementioned staining.

In order to achieve the abovementioned third object, the wafer surface information processing device of the present invention is characterized in that the device is devised so that wafer surface information such as scratch information and staining information for the wafer surface detected by a wafer surface inspection device is accumulated as image information or numerical information, and the sets of accumulated information are superposed so that the trend of generation of scratches and staining in specified processes can easily be detected.

In more concrete terms, the present invention provides the following wafer surface information processing device:

(15) A wafer surface information processing device comprising input means for inputting wafer surface information (scratch information and staining information for the wafer surface) for respective wafers that is supplied from a wafer surface inspection device, memory means for accumulating the abovementioned wafer surface information for each of a plurality of wafers, superposing means for forming superposed surface information by superposing arbitrary wafer surface information accumulated in the abovementioned memory means, display means for displaying the superposed surface information formed by the abovementioned superposing means, and information processing means for processing various types of information.

The term "wafer surface inspection device" refers to a device that detects scattered light that is obtained from the wafer surface when the wafer surface is illuminated with laser light. A commercially device may be used. The main function of this inspection device is to detect respective scattering points (LPD: light point defects) as individual defects.

"Aggregation of LPD (scratches) on the wafer surface" may be either continuous or discontinuous. Furthermore, the arrangement of such aggregation may be either rectilinear or curvilinear. The term "scratches" refers to scratches of various configurations, such as aggregation of defects on the wafer surface, rubbing scratches on the wafer surface and the like.

(16) The wafer surface information processing device according to (15), characterized in that the wafer surface information for each of the abovementioned wafers and the abovementioned superposed surface information are respectively displayed as images on the wafers.

(17) The wafer surface information processing device according to (15) or (16), characterized in that the device is devised so that the judgement of the process in which scratches or staining have been generated can be supported by accumulating the abovementioned wafer surface information in correspondence with wafer history information recording the processes through which each wafer has passed, and outputting wafer surface information corresponding to the abovementioned wafer history information.

(18) The wafer surface information processing device according to (15) or (16), characterized in that the device is devised so that the judgement of the process in which scratches or staining have been generated can be supported by pre-recording the trend of particulars of generated defects for each process through which each wafer passes, and outputting wafer surface information that matches this trend in particulars of generated defects.

A supporting device which is used to support the judgement of the causes of generation of scratches and staining in wafer manufacturing processes, comprising input means, memory means, processing means and output means, characterized in that the abovementioned "wafer surface information corresponding to wafer history information" in wafer surface information processing device according to the subject invention is extracted via the abovementioned input means, the abovementioned extracted "wafer surface information corresponding to wafer history information" is accumulated by the abovementioned memory means, the processes in which scratches and staining are frequently generated are calculated by the abovementioned processing means on the basis of the abovementioned accumulated "wafer surface information corresponding to wafer history information", and the result is output from the abovementioned output means.

The term "frequent occurrence of scratches and staining" includes absolute evaluations indicating occurrence that exceeds specified number of times, relative evaluations indicating occurrence that is more frequent than in other locations, and qualitative evaluations indicating the occurrence of dense or severe scratches and staining even though the number of times of occurrence is the same as in other locations.

A supporting device which is used to support the judgement of the monetary amount to be covered by insurance during the conveyance of wafers, comprising input means, memory means, processing means and output means, characterized in that the abovementioned "wafer surface information corresponding to wafer history information" in the wafer surface information processing device according to (17) is extracted via the abovementioned input means, the abovementioned extracted wafer surface information corresponding to wafer history information" is accumulated by the abovementioned processing means on the basis of the abovementioned accumulated "wafer surface information corresponding to wafer history information", and the result is output from the abovementioned output means.

(21) A computer-readable memory medium which accommodates a program that includes a superposition step in which superposed surface information is formed by superposing wafer surface information (scratch information and staining information for the wafer surface) for each wafer that is supplied from a wafer surface inspection device.

(22) A computer-readable memory medium which accommodates superposed surface information formed by superposing wafer surface information (scratch information and staining information for the wafer surface) for each wafer that is supplied from a wafer surface inspection device.

(23) A computer-readable memory medium which accommodates wafer surface information (scratch information and staining information for the wafer surface) for each wafer that is supplied from a wafer surface inspection device, and superposed surface information that is formed by superposing this wafer surface information.

(24) The memory medium according to (22) or (23), which is a data base that is shared by a plurality of the devices according to any of (15) through (20).

(25) The memory medium according to any of (22) through (24), characterized in that required standards for wafers of specified wafer consumers are further accommodated.

FD, MD, HD and the like may be cited as typical examples of "memory media"; however, a memory medium of any configuration, whether portable or fixed, and whether performing static storage or dynamic storage, may be used, as long as this medium is capable of storing data. Furthermore, the term "specified wafer consumer" refers to a specified customer.

In order to achieve the abovementioned fourth object, the wafer surface information processing device of the present invention is characterized in that the device is devised so that surface information such as scratch information and staining information for the wafer surface that is detected by a wafer surface inspection device is accumulated especially as image information, and so that the trend of the generation of scratches and staining in specified processes can easily be detected by superposing sets of the abovementioned accumulated image information, and the device is further devised so that information regarding this can be shared by the wafer supplier and consumer.

In more concrete terms, the present invention provides the following:

(26) A wafer surface information processing device comprising input means for inputting wafer surface information (scratch information and staining information for the wafer surface) for each wafer that is respectively input from two wafer surface inspection devices, memory means for accumulating the abovementioned wafer surface information for each of a plurality of wafers, superposing means for forming superposed surface information by superposing arbitrary wafer surface information accumulated in the abovementioned memory means, display means for displaying respective sets of wafer surface information or respective sets of superposed surface information of the two wafer surface inspection devices in contrast with each other, and information processing means for processing various types of information.

The term "wafer surface information" typically refers to scratch information and staining information for the wafer surface, but also includes other types of information such as information concerning haze or the like.

Even in cases where a system is constructed by two or more wafer surface inspection devices, this system is included in the scope of the present invention as long as processing similar to that of the wafer surface information processing device of the present invention is performed between the two wafer surface inspection devices.

The term "display in contrast to each other" refers to display methods in which sets of information are displayed in pairs on the screen, display methods in which differences are displayed (such displays may be either image displays or data displays), or the like.

The term "display" refers not only to a display in the form of images, but also includes the display of data in any form.

The term "image display" refers to a display based on images in a CRT or liquid crystal screen, rather than a simple display of data.

The term "wafer surface inspection device" refers to a device which detects scratches and staining on the wafer surface on the basis of an LPD map (defect distribution information for the wafer surface supplied from a particle counter); wafer surface inspection devices that are of the same type, and that have the same performance and approximately the same sensitivity are desirable.

(27) The wafer surface information processing device according to (26), in which the abovementioned wafer surface information and the abovementioned superposed surface information for each wafer are respectively displayed as images on the wafer.

(28) The wafer surface information processing device according to (26) or (27), characterized in that the abovementioned two wafer surface inspection devices are respectively disposed at the starting point and end point of a certain wafer processing process.

(29) The wafer surface information processing device according to (26) or (27), characterized in that the abovementioned two wafer surface inspection devices are respectively disposed on the side of the wafer supplier and on the side of the wafer consumer.

(30) A wafer surface information processing device comprising input means for inputting wafer surface information (scratch information and staining information for the wafer surface) for each wafer that is supplied from a wafer surface inspection device that is disposed following a specified process that treats wafers, memory means for accumulating the abovementioned wafer surface information for each of a plurality of wafers, superposing means for forming superposed surface information by superposing arbitrary wafer surface information accumulated in the abovementioned memory means, recording means for pre-recording the trend of particulars of generated defects in the abovementioned process, and output means for outputting the abovementioned wafer surface information or the abovementioned superposed surface information that matches the abovementioned trend of particulars of generated defects, characterized in that the abovementioned device is devised so that a judgement as to whether or not scratches and staining are generated in the abovementioned process can be performed.

(31) A computer-readable memory medium which accommodates wafer surface information (scratch information and staining information for the wafer surface) for each wafer that is supplied from a plurality of wafer surface inspection devices, and superposed surface information formed by superposing this wafer surface information, and which comprises a data base that is shared by a plurality of wafer surface information processing devices.

FD, MD, HD and the like may be cited as typical examples of "memory media"; however, a memory medium of any configuration, whether portable or fixed, and whether performing static storage or dynamic storage, may be used, as long as this medium is capable of storing data.

(32) A computer-readable memory medium which accommodates wafer surface information (scratch information and staining information for the wafer surface) for each wafer that is supplied from wafer surface inspection devices that are respectively disposed on the side of the wafer supplier and on the side of the wafer consumer, and superposed surface information formed by superposing this wafer surface information, and which comprises a data base that is shared by the wafer supplier and the wafer consumer.

(33) A computer-readable memory medium which accommodates wafer surface information (scratch information and staining information for the wafer surface) for each wafer that is supplied from a wafer surface inspection device that is disposed following a specified process that treats wafers, superposed surface information formed by superposing this wafer surface information, and information which indicates the trend of particulars of generated defects in the process, and which comprises a data base that is shared by a plurality of wafer surface information processing devices.

(34) The wafer surface information processing device according to (29), characterized in that a transmitting device which transmits data for wafers judged to be defective by the wafer consumer is disposed in the wafer surface inspection device located on the side of the wafer consumer.

(35) The wafer surface information processing device according to (29), characterized in that a receiving device which receives data for wafers transmitted by the wafer consumer as a result of the wafers being judged to be defective is disposed in the wafer surface inspection device located on the side of the wafer supplier.

BRIEF DESCRIPTION OF THE DRAWINGS

FIGS. 15(A) and 15(B) are schematic diagrams which are used to illustrate the detection of scratches and criteria for the judgement of defective used in the present invention;

FIG. 25 is a block diagram which shows an embodiment that differs from that shown in FIG. 22.

BEST MODE FOR CARRYING OUT THE INVENTION

The wafer surface inspection device, wafer surface inspection method, defective wafer judgment device, defective wafer judgment method and wafer surface information processing device of the present invention will be described below with reference to the attached figures.

First, the wafer surface inspection device, wafer surface inspection method, defective wafer judgment device and defective wafer judgment method will be described.

Construction of the Apparatus

Figure 1:
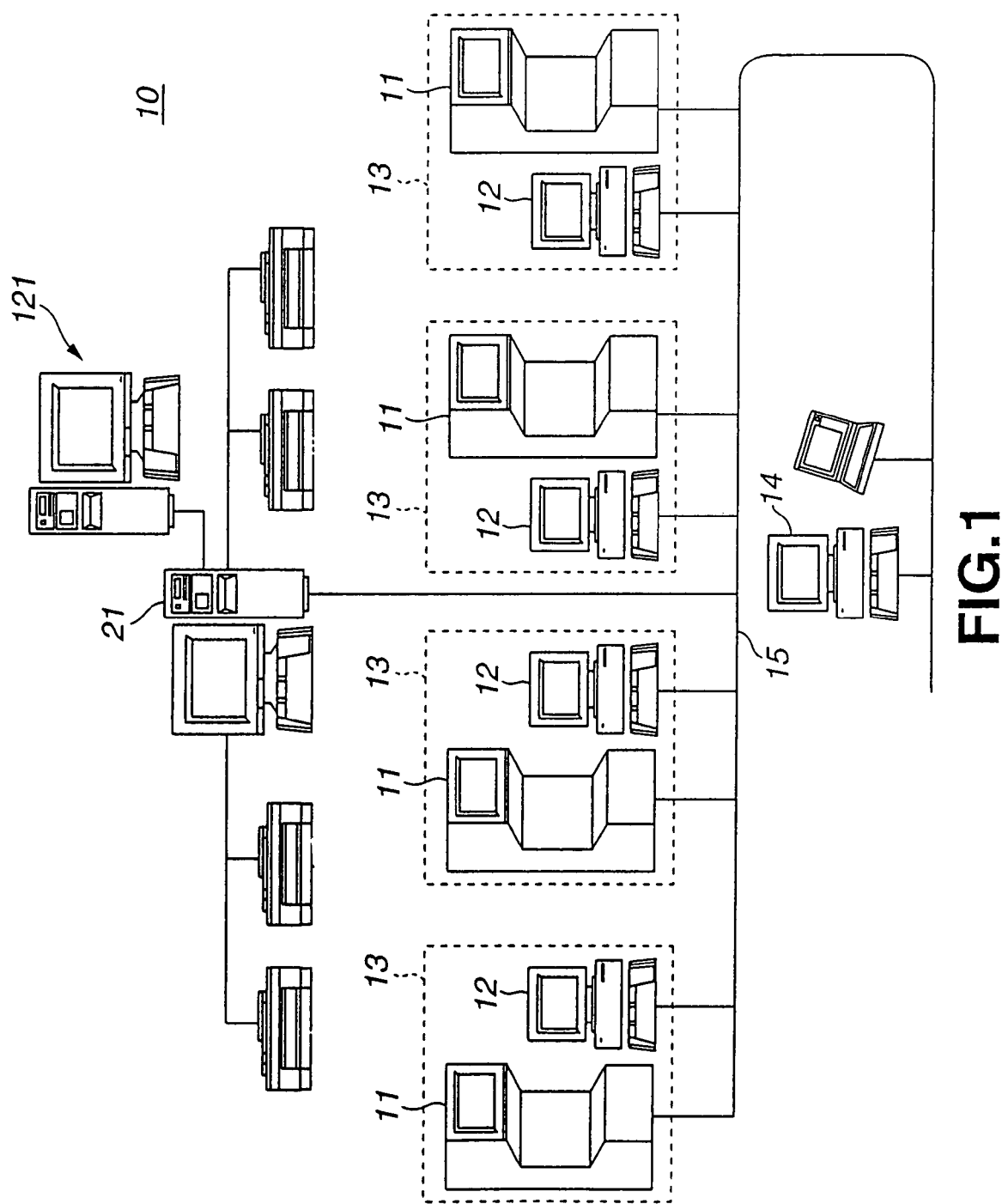
FIG. 1 is a schematic diagram which shows the overall construction of the silicon wafer inspection system of the present invention.

FIG. 1 is a schematic diagram which shows the overall construction of the wafer surface inspection system 10 of the present invention. As is shown in this FIG. 1, the wafer surface inspection system 10 has a plurality of extraction parts 13, each consisting of a laser scattering detector 11 that is used to extract fine defects from the surface of a silicon wafer, and a control computer 12 which is used to control this laser scattering detector 11; furthermore, the system has a judgement computer 21 which gathers the extraction results (LPD map) from the abovementioned extraction parts 13 via a network 15, and judges the status of scratches and staining.

The laser scattering detector 11 of each extraction part 13 illuminates the surface of the silicon wafer with laser light, and detects the scattered light that is generated in cases where defects are present. Then, fine defects in the silicon wafer surface are extracted by producing a map (LPD map: point defect map) in which the respective scattering points detected by the laser scattering detectors 11 are taken as individual defects by gathering the coordinate values in a predetermined coordinate system on the wafer and the intensity values of the scattered light.

Information (i.e., the LPD map) concerning the individual scattering points (defects) on the silicon wafer surface that are thus extracted is stored in correspondence with the wafer ID, slot number or the like on a hard disk installed in each laser scattering detector 11, or is stored directly on the hard disk of the judgement computer 21 via the network 15.

The judgement computer 21 acquires the wafer IDs and slot numbers of the silicon wafers that are to be judged from the respective control computers 12, and scattering point information (LPD map) corresponding to these wafer IDs and slot numbers from the corresponding laser scattering detectors 11 via an LAN (local area network) (network 15) constructed from an ether net.

Even in cases where a plurality of control computers 12 and laser scattering detectors 11 control LPD maps using different formats, the system is devised so that the judgement computer 21 that has acquired this information converts the information into a common format for handling.

Furthermore, a supporting device 121 with a computer construction that is used to detect constantly occurring defects by superposing surface information (described later) expressing cracks and staining is connected to the judgement computer 21.

Figure 2:
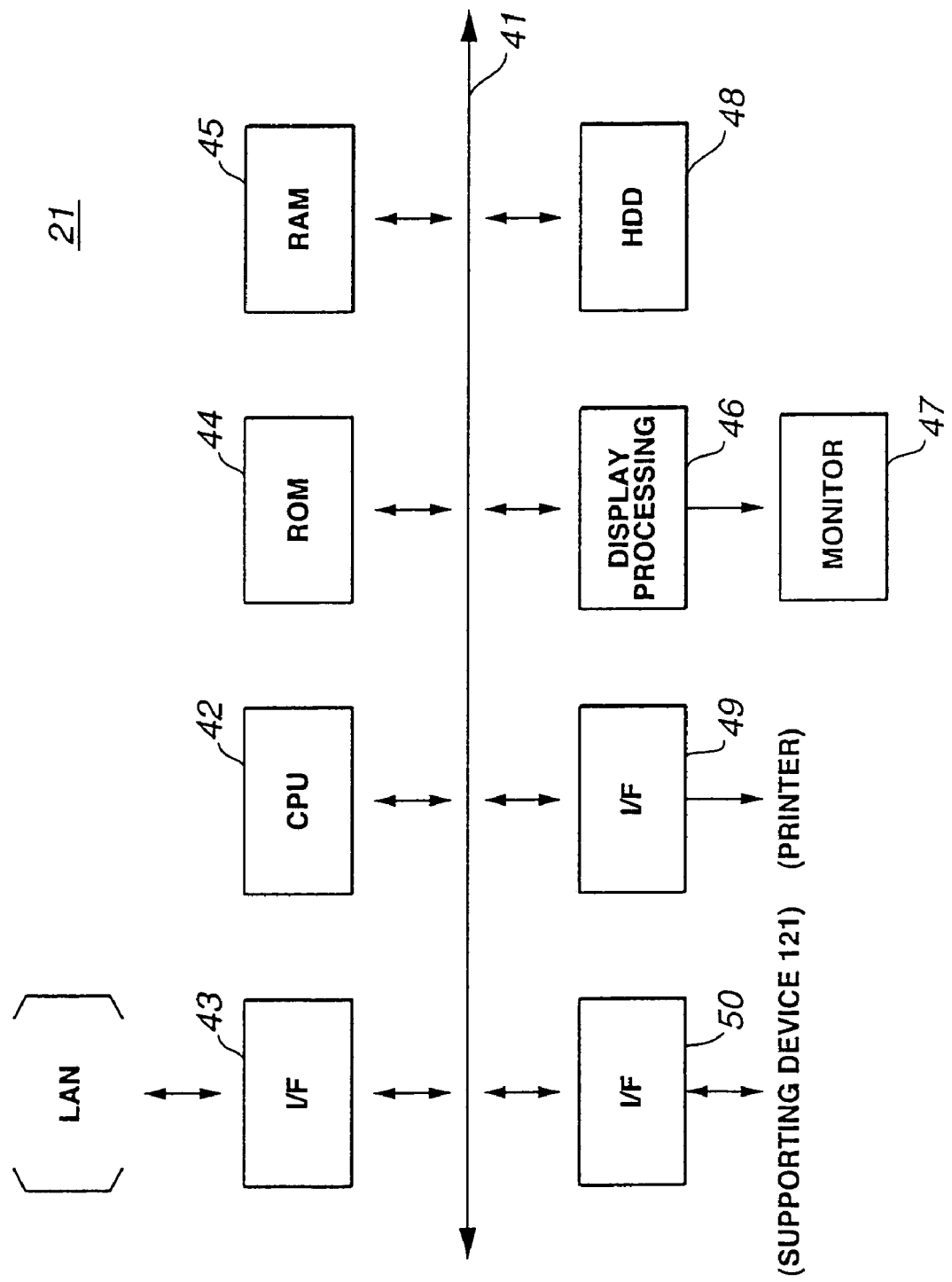
FIG. 2 is a block diagram which shows the construction of the defect judging computer of the present invention.
Figure 24:
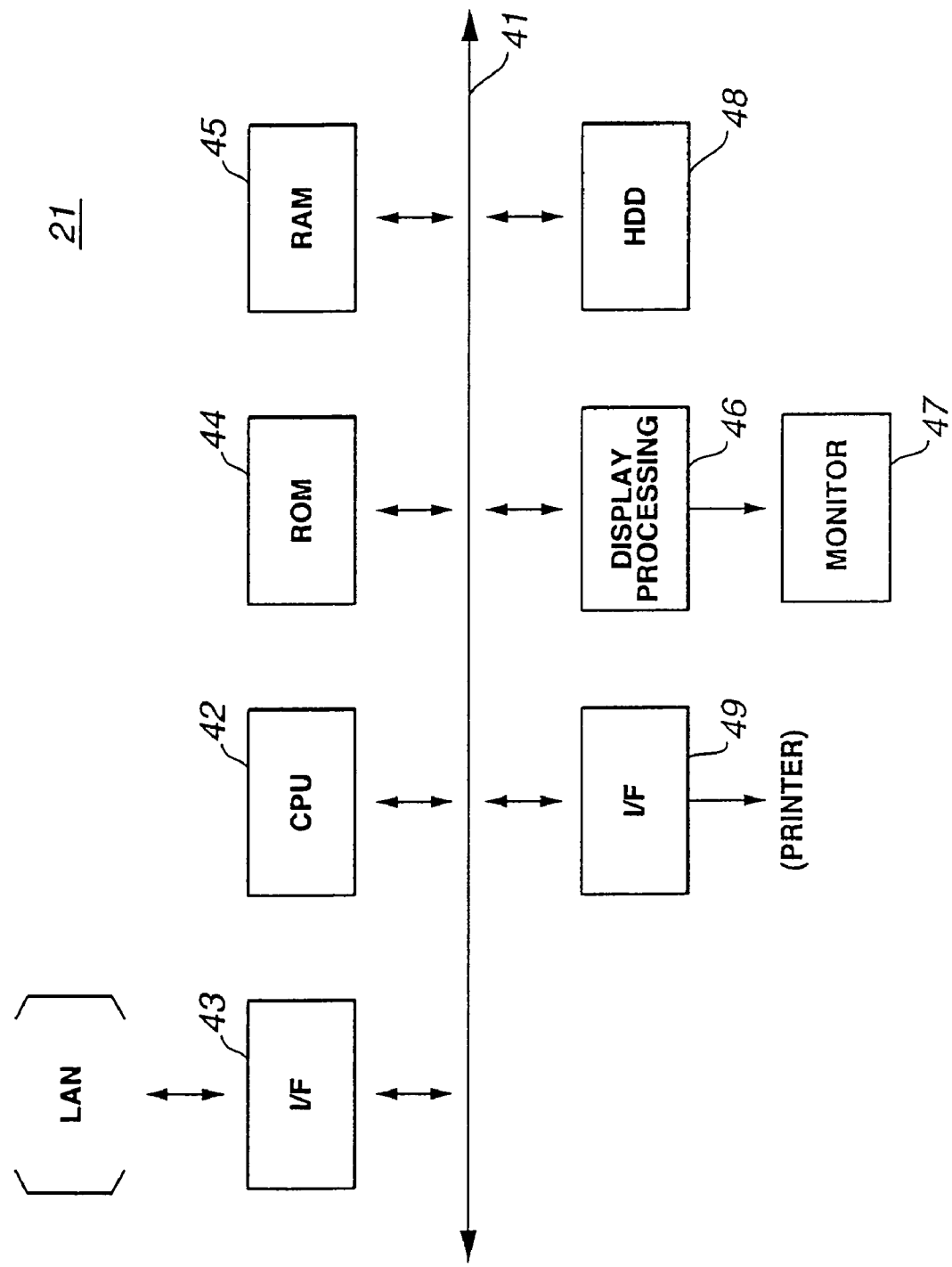
FIG. 24 is a block diagram which shows the construction of computer used to judge defects that differs from the computer shown in FIG. 2.

Here, FIG. 2 is a block diagram which shows the construction of the judgement computer 21, in which a CPU (central processing unit) 42, a ROM (read-only memory) 44, a RAM (random-access memory) 45, a hard disk drive 48, a display processing part 46, and interfaces 43, 49 and 50, are connected via a bus 41. Furthermore, in cases where no supporting device 121 is connected to the judgement computer 21, the interface 50 is not connected to the bus 41 (as is shown in FIG. 24).

The CPU 42 operates in accordance with a program that is stored in the ROM 44, or a program that is read out from some other memory medium; this CPU receives scattering point information (LPD maps) for respective silicon wafers supplied from the laser scattering detectors 11 and control computers 12 via the interface 43, and stores this information in the hard disk of the hard disk drive 48.

The CPU 42 writes specified portions of the LPD maps stored on the hard disk into the RAM 45 as required, and performs scratch and staining extraction processing and acceptability judgement processing (described later). The results of this processing are visually displayed on a monitor 47 such as a CRT (cathode ray tube) or the like after graphic processing is performed in the display processing part 46; if necessary, furthermore, the processing results are supplied to a printer via the interface 49 (such as a USB terminal or the like), and are printed out.

Figure 3:
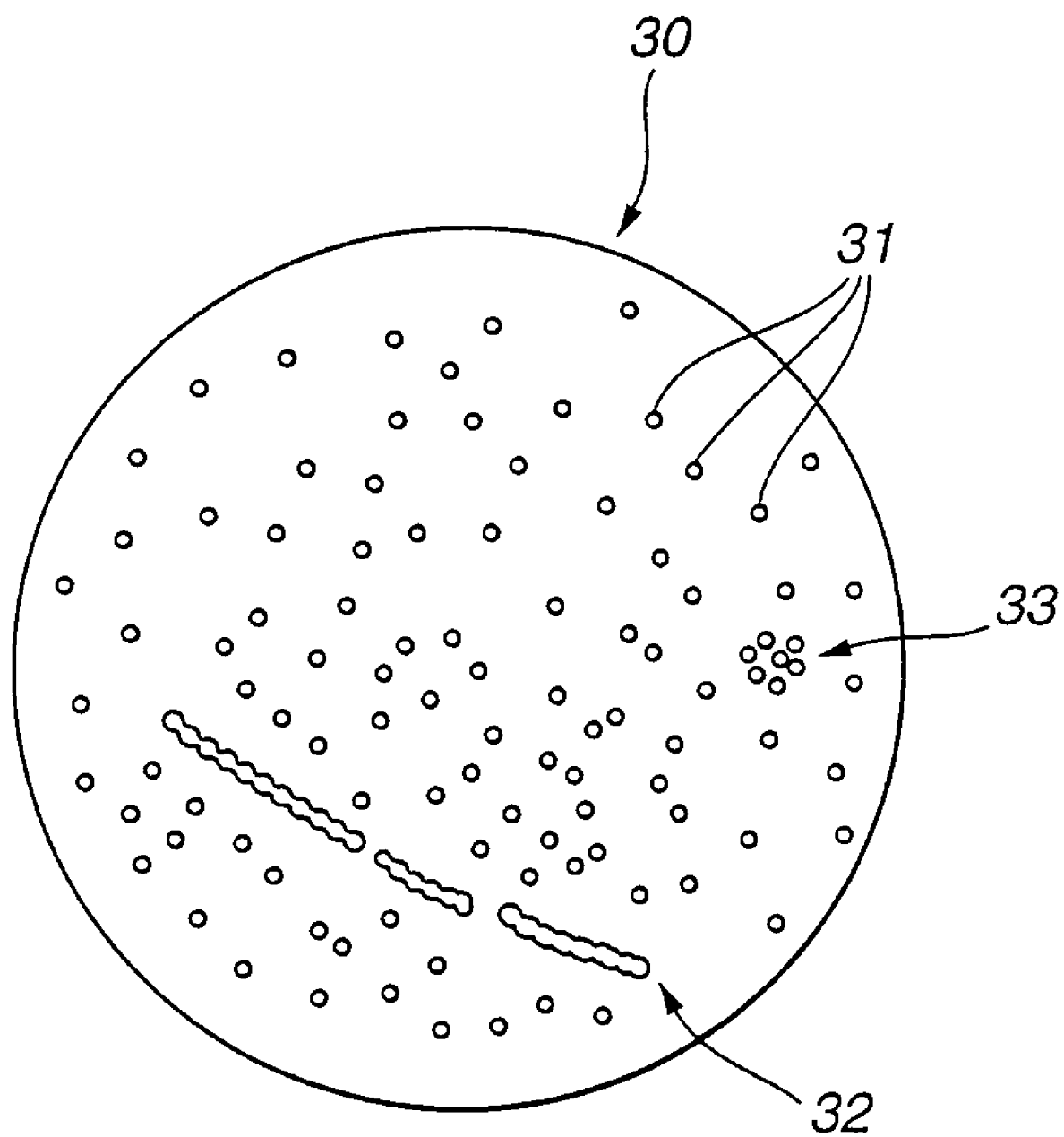
FIG. 3 is a schematic diagram which shows an example of LPD map detection.

Here, FIG. 3 shows a display example in which the LPD map 30 supplied to the judgement computer 21 from the laser scattering detector 11 is converted into image information and displayed. The system is devised so that the judgement computer 21 detects scratches and staining that may constitute defects in accordance with the conditions of aggregation (characterizing quantities) of the plurality of scattering points 31 generated on the surface of the silicon wafer. For example, among the plurality of scattering points shown in FIG. 3, continuous aggregate areas 32 of scattering points that are approximately linear are detected as scratches, and indefinite-form aggregate areas 33 of scattering points that have a high density are detected as staining.

Figure 4:
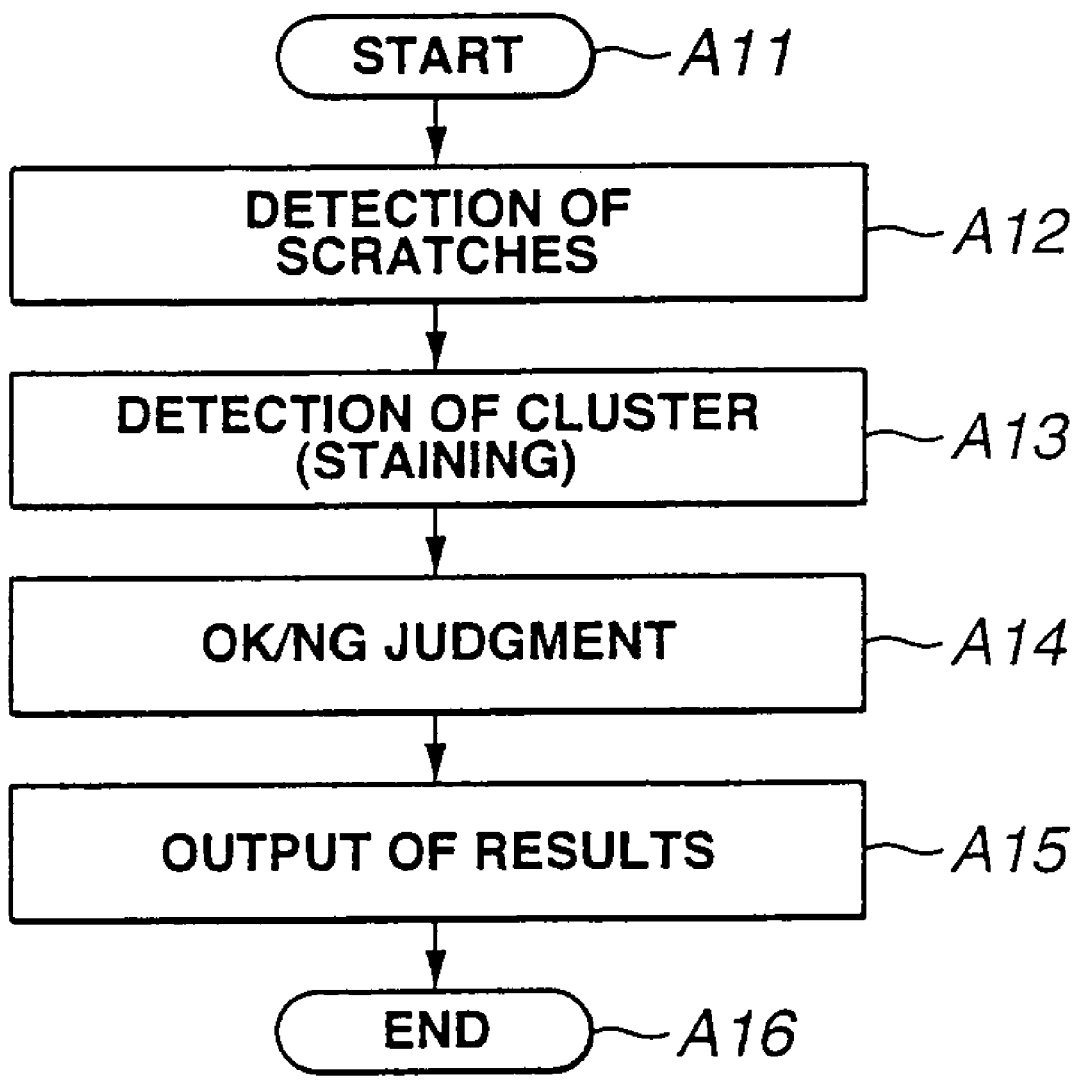
FIG. 4 is a flow chart which shows the silicon wafer surface inspection processing routine of the present invention.

More specifically, according to the inspection processing routine as shown in FIG. 4, the judgement computer 21 is devised to detect linear scratches and indefinite-form staining from the conditions of generation of cluster and aggregates of scattering points 31 on the surface of a silicon wafer and to judge whether or not such scratches and staining should be determined as defects on the basis of the conditions of generation of cluster and aggregates of the scattering points 31 (characterizing quantities) judge obtained as the detection results. Upon acquiring LPD map data from the laser scattering detectors 11, the judgement computer 21 first enters the inspection processing routine from step A11. In step A12, linear aggregate areas 32 of scattering points 31 on the silicon wafer surface are detected from the LPD map by an interval analysis method and pyramid processing, and these areas are recognized as scratches.

Then, when the scratch detection processing in step A12 is completed, the judgement computer 21 proceeds to the following step A13, and detects any cluster consisting of indefinite form aggregation of scattering points, i.e., staining on the silicon wafer surface, from the LPD map.

When scratches and staining are detected, the judgement computer 21 proceeds to step A14; here, the judgement computer 21 classifies the type of the detected scratches and staining on the basis of characterizing quantities relating to these scratches and staining, and uses judgement criteria based on the results of this classification to judge whether or not the silicon wafer that is the object of inspection in this case is to be designated as "defective". The results of this judgement are output to a printer or the like in step A15, after which the inspection processing routine is completed in step A16.

Figure 5A:
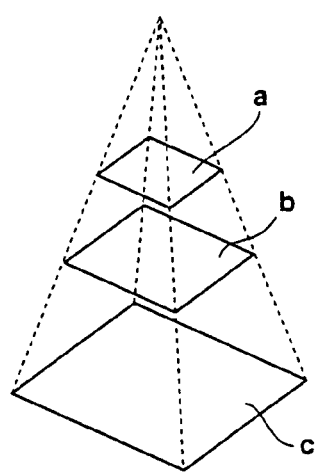
FIGS. 5(A) to 5(D) are schematic diagrams which are used to illustrate pyramid processing in the scratch detection processing of the present invention.

Here, the details of the scratch detection processing in the abovementioned step A12 will be described. FIGS. 5(A) to 5(D) show schematic diagrams which are used to illustrate the pyramid processing that is performed when cluster and aggregate areas of scattering points 31 that may result in a judgement of "defective" are detected from the LPD map 30. Here, as shown in FIG. 5(A), the judgement computer 21 extracts linear aggregate areas of scattering points by performing interval analysis processing (described later) at respective resolutions using three stages of resolution (a: 200×200 [dots], b: 400×400 [dots], c: 1000×1000 [dots]) on the LPD map 30 written into the RAM 45.

Figure 5B:
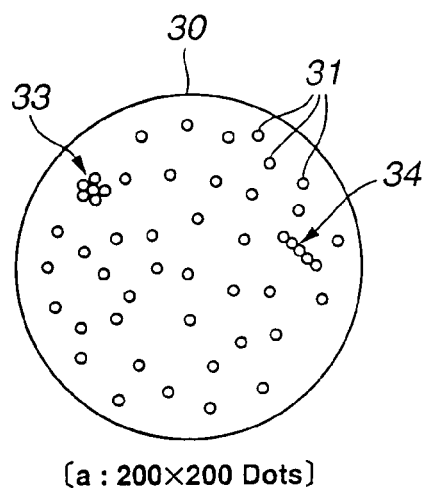

Specifically, the judgement computer 21 first subjects the LPD map 30 to image analysis at a low resolution (a: 200×200 [dots]) as shown in FIG. 5(B), and extracts cluster 33 and linear aggregate areas 34 of scattering points 31. In this case, the linear aggregate areas 34 of scattering points that can be extracted at this resolution are detected as scratches at this resolution by the rotational projection method (described later).

Figure 5C:
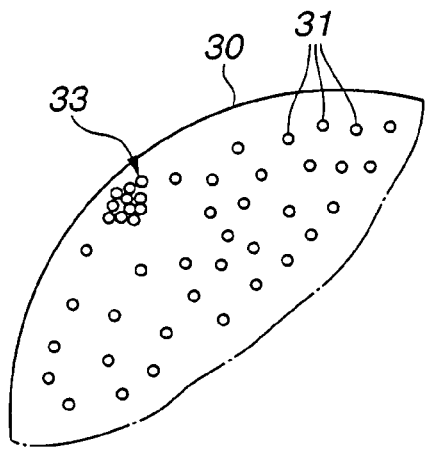
Figure 5D:
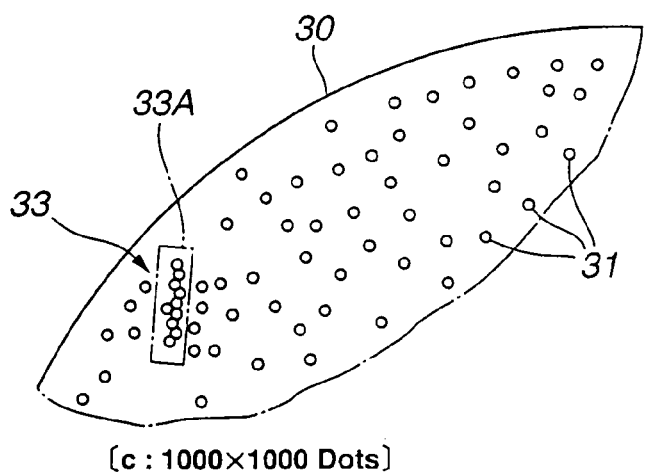

When the detection processing at a low resolution is completed, the judgement computer 21 performs image analysis at a somewhat higher intermediate resolution (b: 400×400 [dots]) as shown in FIG. 5(C), and extracts cluster 33 and linear aggregate areas of scattering points 31. In this case, the linear aggregate areas of scattering points that can be extracted at this resolution are detected as scratches by a rotational projection method (described later) at the same resolution. Incidentally, in the case of the LPD map 30 shown in FIG. 5(C), cluster 33 of scattering points are recognized, but linear aggregate areas are not recognized. In such a case, it is possible that linear aggregate areas of scattering points that can be extracted at an even higher resolution are present within the cluster 33. Accordingly, as is shown in FIG. 5(D), the judgement computer 21 subjects the LPD map 30 to image analysis at an even higher resolution (c: 1000×1000 [dots]), and extracts cluster 33 and linear aggregate areas. In the case of the LPD map 30 shown in FIG. 5(C), cluster 33 of scattering points are recognized, but no linear aggregate areas are recognized. In such a case, it is possible that linear aggregate areas of scattering points that can be extracted at a higher resolution are present within the cluster 33; accordingly, as is shown in FIG. 5(D), the judgement computer 21 subjects the LPD map 30 to image analysis at an even higher resolution (c: 1000×1000 [dots]) and extracts the cluster 33 and linear aggregate areas.

In the LPD map 30 at the high resolution shown in FIG. 5(D), linear aggregate areas 33A that were hidden in the cluster 33 (which are high-density areas of scattering points 31) at a low resolution are recognized, so that the judgement computer 21 can detect these aggregate areas 33A for the first time by a rotational projection method (described later) at this resolution.

Figure 6:
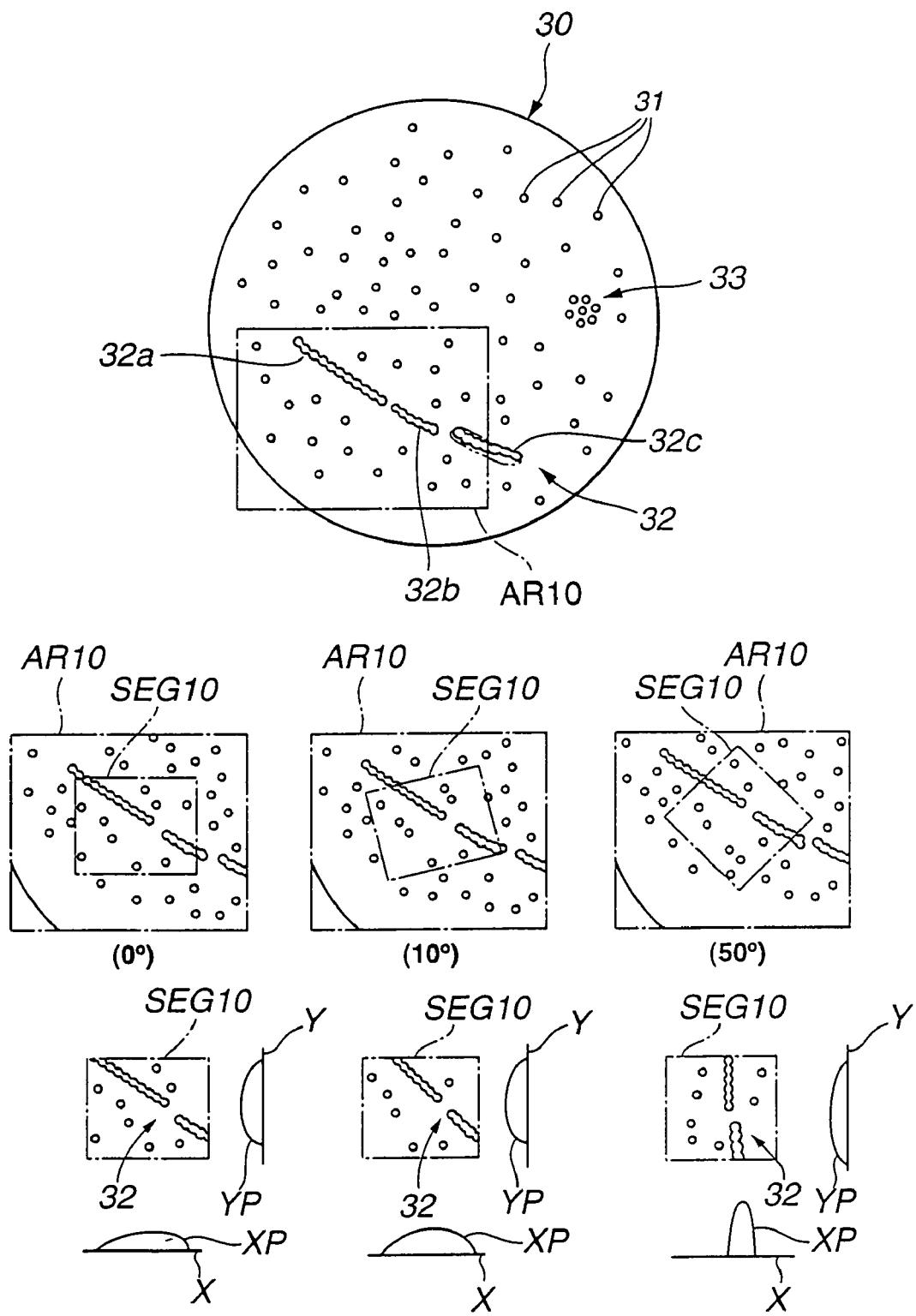
FIG. 6 is a schematic diagram which is used to illustrate the rotational projection method in the scratch detection processing of the present invention.

Next, the method used to detect linear aggregate areas of scattering points by an interval analysis method using a rotation projection method performed by the judgement computer 21 at various resolutions will be described. FIG. 6 is a schematic diagram which illustrates the principle of the method used to detect linear aggregate areas of scattering points that may constitute defective linear scratches. Here, a segment SEG10 is cut out from a specified area AR10 of the LPD map 30 prepared on the basis of the scattering points 31 on the surface of the silicon wafer, and this segment SEG10 is rotated. As for the method used to rotate the segment SEG10, a method such as altering the image data read-out address in accordance with the rotational angle on the basis of the image data for the area AR10 extracted in the RAM 45 (FIG. 2), and then reading out this data, is used.

The results obtained by projecting the respective scattering points 31 onto the vertical axis (Y axis) of the segment SEG10 in this case are designated as the Y axis projection curve YP, and the results obtained by projecting the respective scattering points 31 onto the horizontal axis (X axis) of the segment SEG10 in this case are designated as the X axis projection curve XP.

The abovementioned X axis projection curve XP and Y axis projection curve YP assume larger values as the quantity of scattering points (number of scattering points) projected onto the respective axes increased. Accordingly, in the case of the segment SEG10 at a rotational angle of 50° as shown in FIG. 6, the value of the X axis projection curve XP is partially increased in a state in which the angle formed by the direction of length of the continuous aggregate area 32 among the scattering points present inside the segment and the X axis of the segment SEG10 is substantially a right angle.

Accordingly, when a state in which the X axis projection curve XP and Y axis projection curve YP show a partially steep rise is detected, it is ascertained that a continuous aggregate area 32 of scattering points is present. This means that the aggregate area 32 of the scattering points is detected even if this area is not continuous, so that a state in which scattering points are at least lined up with regularity in a fixed direction can be detected within the segment SEG10. FIG. 6 shows state in which the rotational angles are 0°, 10° and 50°; however, in the method of the present embodiment that is used to detect aggregate areas 32 of scattering points using the abovementioned rotational projection method, the direction of the rotational projection is not fixed; aggregate areas 32 of scattering points can be detected regardless of the orientation of these areas by observing the conditions of the rise in the X axis projection curve XP and Y axis projection curve YP when continuously rotated.

Figure 7:
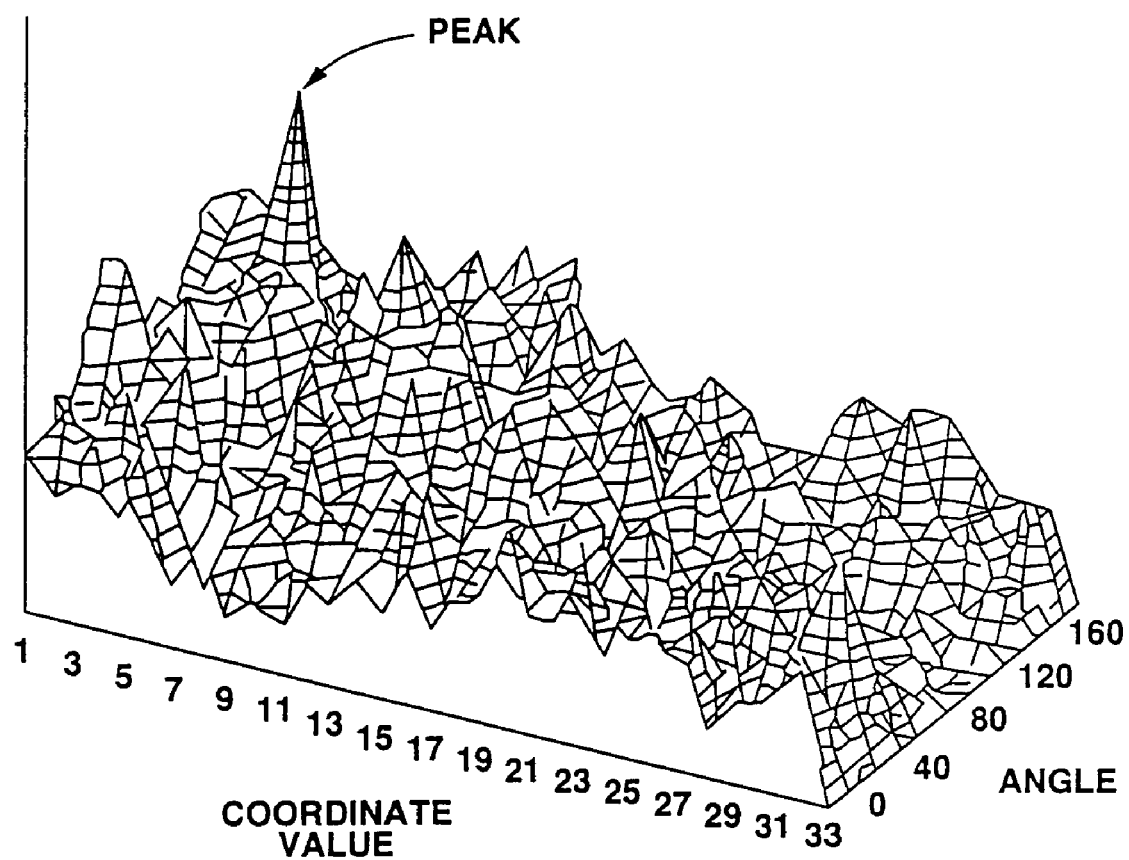
FIG. 7 is a schematic diagram which is used to illustrate the rotational projection method in the scratch detection processing of the present invention.

Here, FIG. 6 shows the principle of detection of the abovementioned detection method used to detect continuous linear aggregate areas 32 of scattering points by means of the abovementioned projection curves. In actuality, however, linear aggregate areas 32 of scattering points can be judged by lining up histograms for the X axis projection curve XP and Y axis projection curve YP in correspondence with the respective rotational angles, and finding the peak, as shown in FIG. 7. This judgement method uses a straight line detection method base on a so-called two-dimensional half conversion.

Thus, the judgement computer 21 detects linear aggregate areas of scattering points that may be cause for a judgement of "defective" through the entire area of the silicon wafer by means of the rotational projection method shown in FIGS. 6 and 7 for each resolution shown in FIGS. 5(A) to 5(D). In the case of linear aggregate areas of scattering points shows position (segment SEG10) is specified by the rotational projection method, the judgement computer 21 recognizes these areas a linear scratches by image processing based on the brightness and color of the areas, and retains this image information and numerical information that expresses the positions and shapes of areas recognized as scratches as wafer surface information.

Here, for example, in a case where three blocks 32a, 32b and 32c are recognized by the CPU 42 as linear scratches as shown in FIG. 6, it is necessary to make a judgement as to whether these three blocks 32a, 32b and 32c should be taken as a single scratch or as a plurality of scratches (two or three scratches). Accordingly, in the abovementioned step A12 (FIG. 4), the judgement computer performs processing that connects the recognized linear scratches under fixed conditions.

Figure 8:
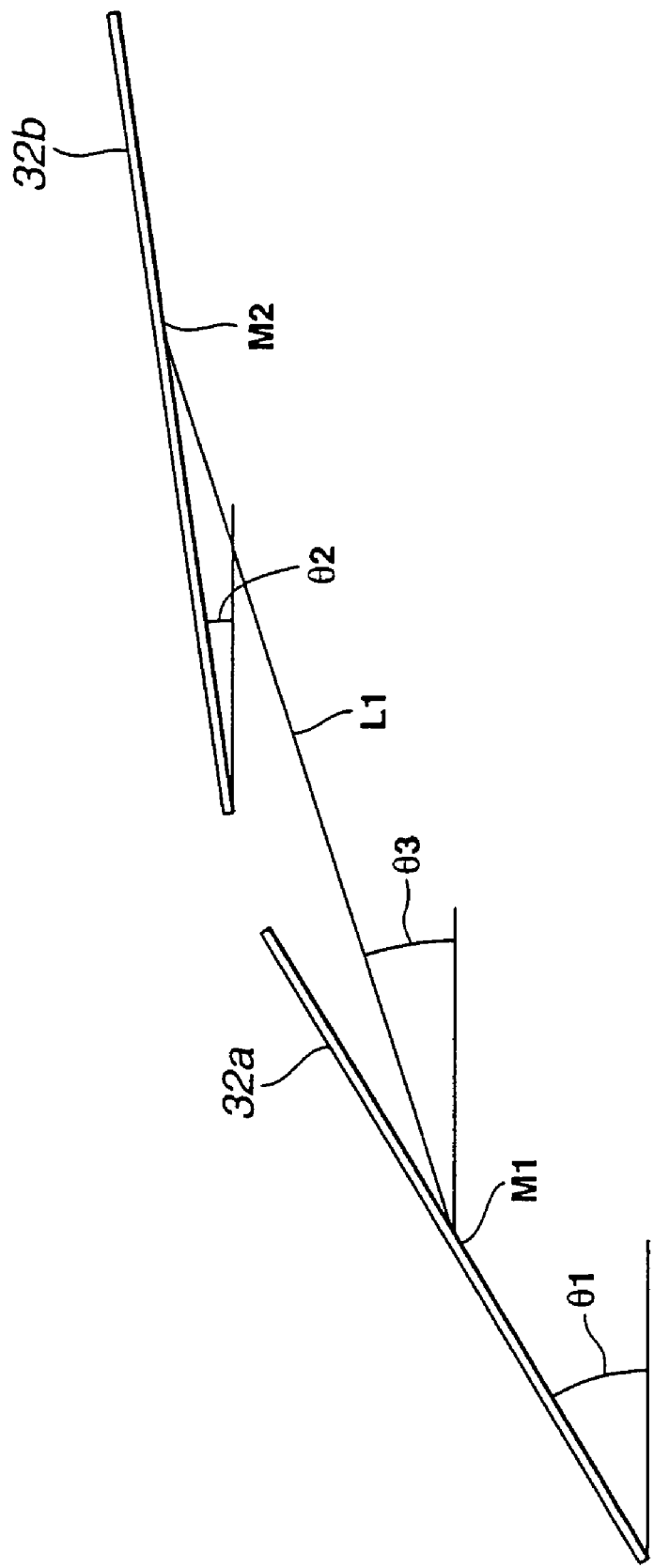
FIG. 8 is a schematic diagram which is used to illustrate the scratch reproduction method of the present invention.

Specifically, as is shown in FIG. 8, the following method is used as a method for judging whether or not the first block 32a and second block 32b recognized as linear scratches are viewed as a single scratch: namely, the judgement computer 21 determines the degree of angular similarity Z by means of the following formula using the angles θ1 and θ2 of the two scratch blocks 32a and 32b with respect to a reference direction, and the angle θ3 of a straight line L1 connecting the midpoints M1 and M2 of the respective blocks 32a and 32b with respect to the abovementioned reference direction:

$$Z=|\cos(\theta_1-\theta_2)||\cos(\theta_2-\theta_3)||\cos(\theta_3-\theta_1)|$$

This formula determines the internal product of the differences in the respective angles; as the degree of angular similarity Z approaches 1, the degree of connectedness of the two blocks 32a and 32b, i.e., the degree to which these blocks are to be connected, increases.

This means that it is judged that these two blocks 32a and 32b are to be connected on the condition that the angles θ1 and θ2 of the two blocks 32a and 32b are in close proximity to each other, and the condition that the two blocks 32a and 32b are not separated at right angles (i.e., the condition that the angle θ3 is small). However, even in cases where it is judged that the degree of connectedness is high in this formula, these blocks are not to be connected if the gap between the two blocks 32a and 32b is large. Here, the judgement computer 21 uses the method shown in FIG. 9 in order to judge whether or not the two blocks 32a and 32b are to be connected.

Figure 9:
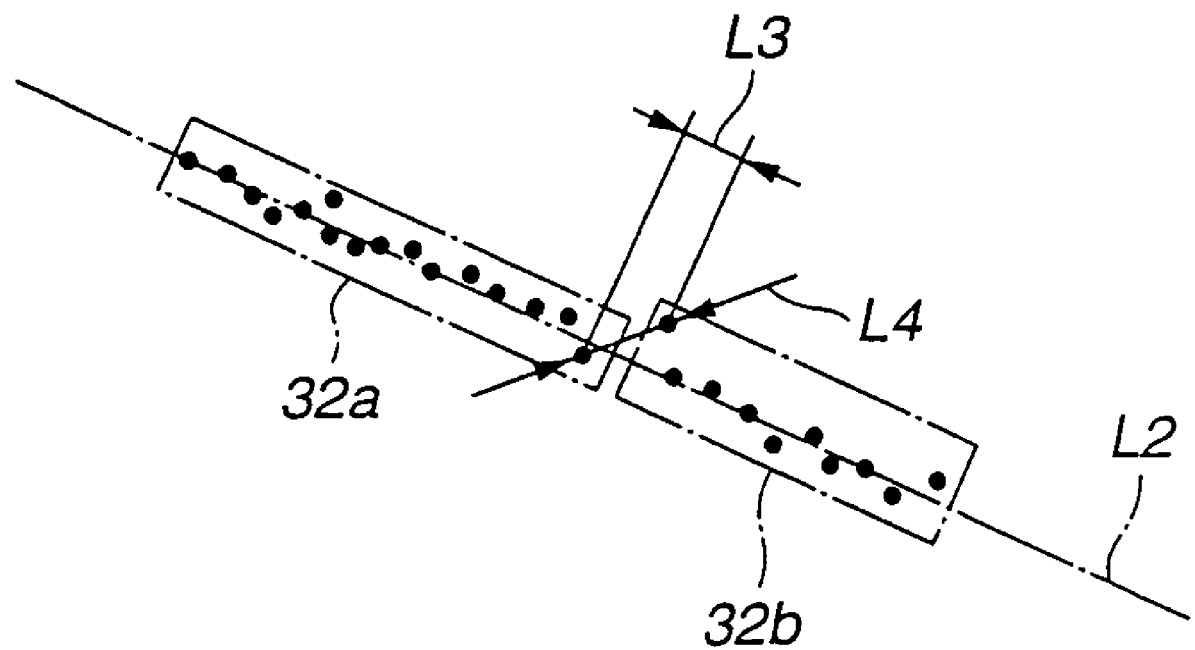
FIG. 9 is a schematic diagram which is used to illustrate the scratch reproduction method of the present invention.

Specifically, in FIG. 9, the judgement computer 21 draws an approximate straight line L2 that is common to the two blocks 32a and 32b, and in cases where the spacing L3 of the two blocks 32a and 32b in the direction of the approximate straight line L2 is smaller than a specified predetermined value, the judgement computer 21 judges that the two blocks 32a and 32b are to be connected.

By thus judging the necessity of connection on the basis of the spacing L3 of the two blocks 32a and 32b in the direction of the approximate straight line L2, it is possible to connect two blocks 32a and 32b that are in close proximity to each other (and that are to be connected) with greater reliability than in a case where this judgement is based on the distance L4 between the closest two points of the blocks 32a and 32b.

Figure 10A:
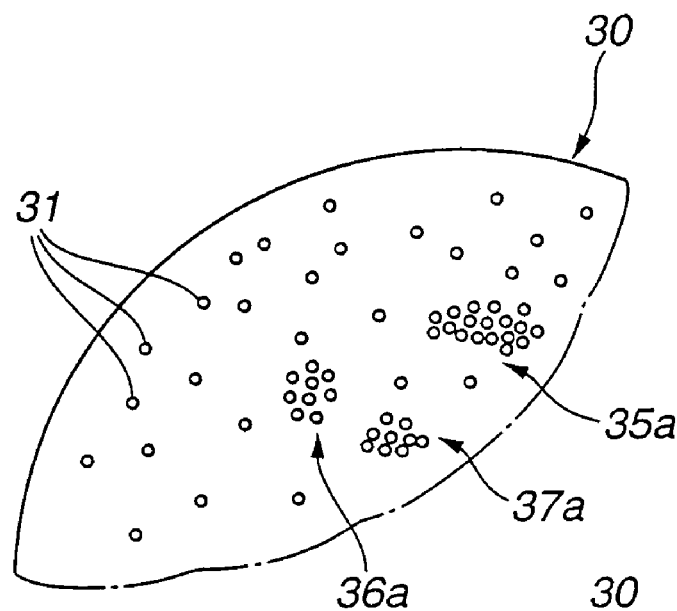
FIGS. 10(A) to 10(C) are schematic diagrams which are used to illustrate the staining reproduction method of the present invention.
Figure 11A:
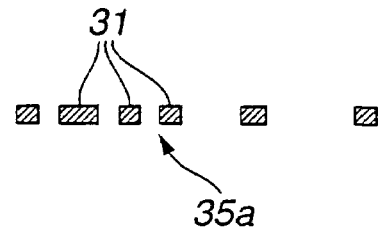
FIGS. 11(A) to 11(D) are schematic diagrams which are used to illustrate the staining reproduction method of the present invention.
Figure 11B:
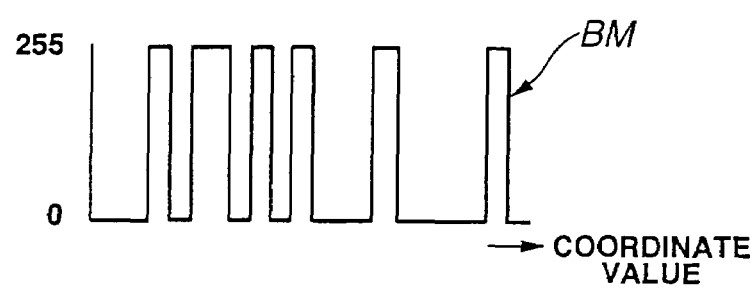

Next, the detailed processing routine in the detection processing step A13 that detects the cluster of scattering points 31 (staining) on the silicon wafer surface shown in FIG. 4 will be described. FIG. 10(A) shows an LPD map 30 which indicates the conditions of detection of scattering points 31 on the surface of the silicon wafer. This figure shows a state in which clustered areas 35a, 36a and 37a of scattering points 31 are present. In this state, the scattering points 31 on the LPD map 30 are expressed as dots such as those shown in FIG. 11 (A). The respective dots on such an LPD map 30 are subjected to conversion processing into (for example) a 256-gradation bit map by the judgement computer 21, thus producing bit map data BM such as that shown in FIG. 11(B).

Figure 10B:
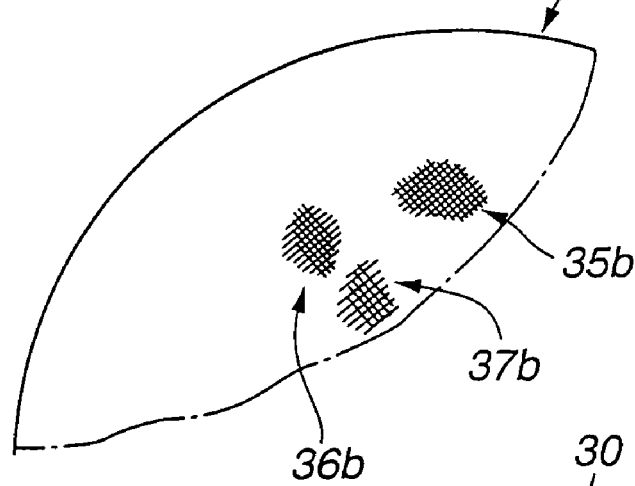
Figure 10C:
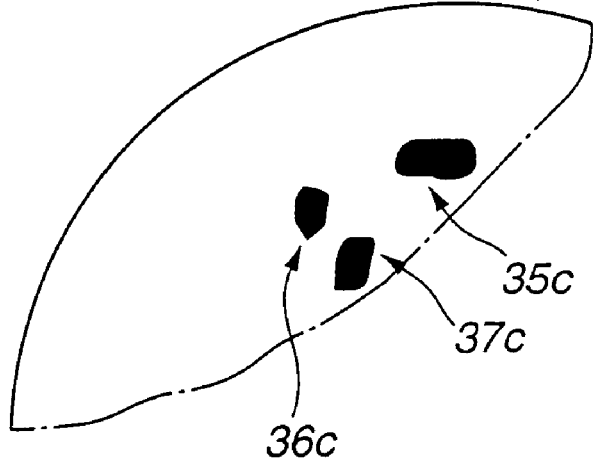
Figure 11C:
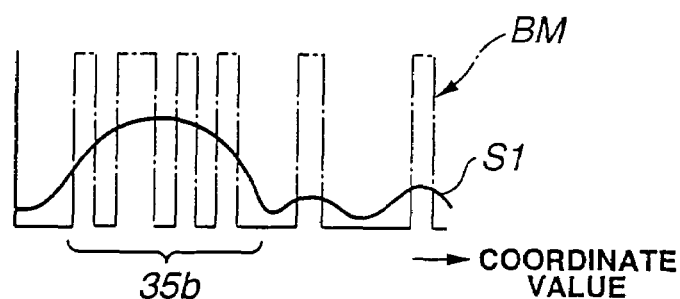
Figure 11D:
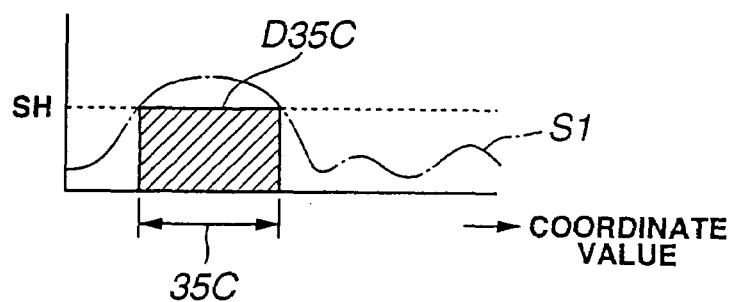

The judgement computer 21 performs smoothing of the bit map data BM using a space filter, so that a smoothed curve S1 formed by smoothing the bit map data BM is obtained as shown in FIG. 11(C). When such a smoothed curve S1 is expressed as an image. Only the clustered areas 35b, 36b, and 37b of the scattering points 31 are expressed in a state in which the surrounding areas are indistinct as shown in FIG. 10 (B). In this display state, as a result of the smoothing processing, those dots that are separated from other dots are expressed with a lighter color.

Then, as shown in FIG. 11 (D), the judgement computer 21 obtains binarized area data D35C by binarizing such a smooth curve S1 suing a preset threshold value SH. Clustered areas 35c, 36c, and 37c with a brightness that is distinctly different from that of the surrounding areas (as shown in FIG. 10 (C)) are obtained by means of this binarized are data D35C. By thus extracting the clustered areas of the scattering points 31 with a set threshold value SH, it is possible to extract these clustered areas in a reliable manner by selecting the threshold value SH, even in cases where these clustered areas are areas in which the degree of concentration of the scattering points is only slightly higher than in surrounding areas.

Furthermore, by thus appropriately varying the threshold value SH that is used when the binarized data D35C is obtained, it is possible to detect cluster areas corresponding to the detected state of the scattering points 31 (overall density of the scattering points 31) on the silicon wafer surface. For example, in cases where large numbers of scattering points 31 are detected overall, it is possible to detect areas with an especially high detection density as clustered areas in distinction from other areas in which an average number of scattering points 31 are present by setting the threshold value SH at a high level. Furthermore, the judgement computer 21 recognizes indefinite-form clustered areas that are detected in this way as staining, and retains these areas in the form of image information and numerical information expressing position, shape and the like (wafer surface information).

When scratches and staining on the silicon wafer surface are thus detected, the judgement computer 21 determines whether or not these detected scratches and staining are cause for a judgement of "defective" in the processing step A14 shown in FIG. 4.

Specifically, the system is arranged so that in the case of linear scratches extracted in step A12 shown in FIG. 4, the judgement computer 21 determines whether or not these scratches are cause for a judgement of "defective" on the basis of the length and detected intensity of the scratches. In this case, the length of the scratches refers to the length of scratches recognized as single scratches by the method described above with reference to FIGS. 8 and 9. Furthermore, the detected intensity refers to the peak value PEAK (corresponding to the depth of the scratches) of the projection curves XP and YP (histograms) in the rotational projection method described above with reference to FIGS. 6 and 7.

Figure 12:
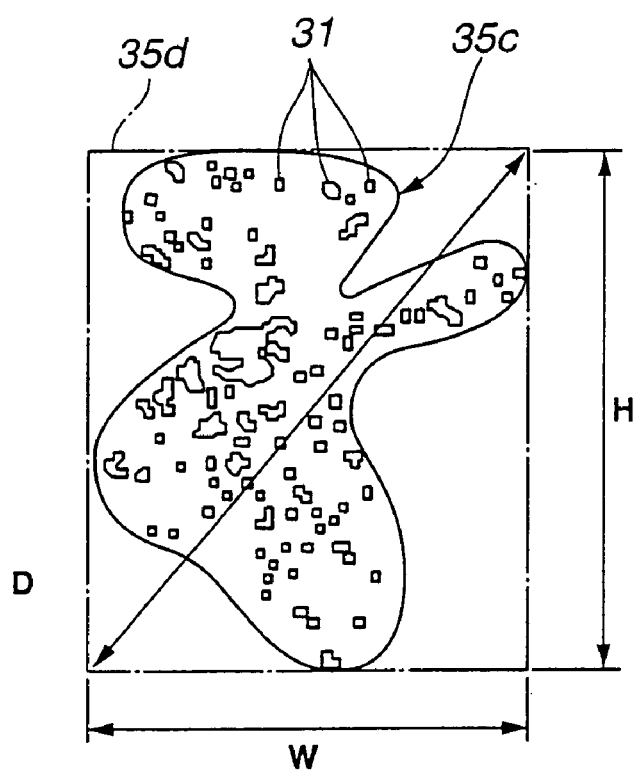
FIG. 12 is a schematic diagram which is used to illustrate the staining reproduction method of the present invention.

Furthermore, in the case of cluster (staining) extracted in step A13 shown in FIG. 4, the system is devised so that the judgement computer 21 determines a circumscribed square shape, and determines whether or not such staining is cause for a judgement of "defective" on the basis of the area of this circumscribed square shape, the length in the longitudinal direction, the length in the lateral direction, the length of the diagonal, the density and the area-density judgement curve. Specifically, as is shown in FIG. 12, for a clustered (staining) area 35c extracted in the abovementioned step A13, the judgement computer 21 determines a circumscribed square shape 35d for this area 35c, measures the length H in the longitudinal direction, length W in the lateral direction, length D of the diagonal and area of this circumscribed square shape 35d, and further determines the density on the bases of the integrated value of the respective scattering points 31 in the clustered (staining) area 35c.

Then, on the basis of the area and density of the circumscribed square shape 35d, the judgement computer 21 renders a judgement of "defective" in cases where an area-density judgement formula expressed by (density−asymptotic density)>coefficient α/(area−asymptotic area) is satisfied. This means that a judgement of "defective" is rendered in cases where the values of the density and/or area are greater than those of the area-density judgement curve S35 shown in FIG. 13. Specifically, it is noted that an inversely proportional relationship between the area and density is taken as a condition for the determination of staining by human inspection; the abovementioned area-density judgement formula expresses this fact as a conditional formula. By using this conditional formula, it is possible to determine (under the same conditions) "defective" status resulting from staining that has conventionally been determined by human observation.

Figure 14:
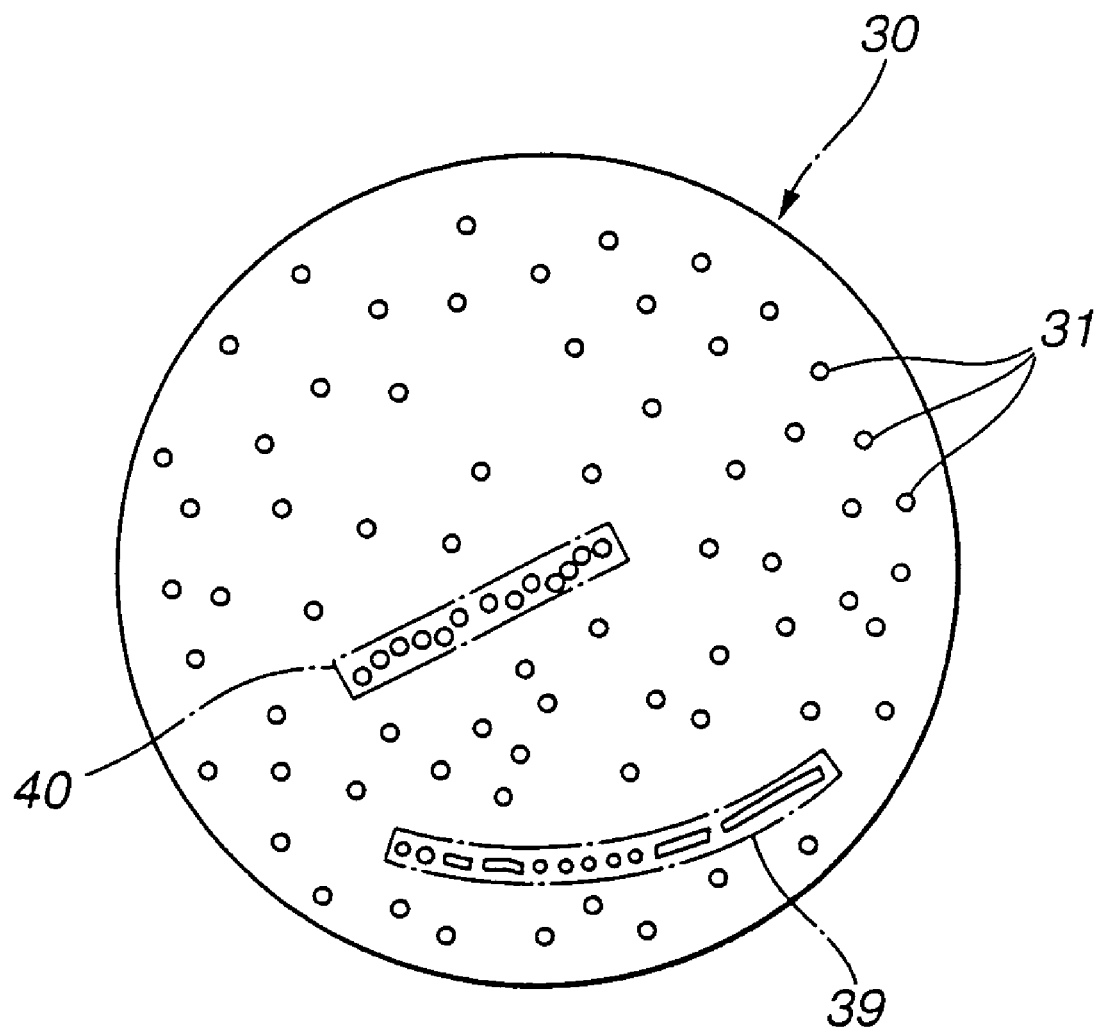
FIG. 14 is a schematic diagram which is used to illustrate the types of scratches involved in the present invention.

In addition to the basic judgement method for determining "defective" status on the basis of such scratches and staining, the judgement computer 21 also classifies types of scratches and staining according to characterizing quantities of the concentrated areas and clustered areas of the scattering points, and sets criteria for the judgement of "defective" status in accordance with the results of this classification. Specifically, as is shown in FIG. 14, the scratches formed on the surface of the silicon wafer include (for example) a regular sequence of circular arc form scratches 39 generated in the lapping process (this sequence is referred to below as the "first scratch"), and an irregular sequence of scratches 40 consisting of an aggregation of defects called "pock marks" that accompany a deterioration in the electrical pressure resistance (GOP) (this sequence is referred to below as the "second scratch"). Here, it is necessary that the second scratch 40 be judged to be a more serious defect than the first scratch 39.

Accordingly, the system is devised so that in the judgement processing step A14 shown in FIG. 4, the judgement computer 21 judges the types of the scratches in accordance with the aggregate state (characterizing quantities) of the scattering points, and varies the judgement criteria in accordance with the type of scratch in question. For example, in the case of the second scratch, in which the arrangement of the scattering points constituting a characterizing quantity is relative irregular, the length that serves as a judgement criterion is shortened compared to that used in the case of the first scratch (in which the arrangement of the scattering points that constitutes a characterizing quantity is relatively regular), so that a judgement of "defective" is rendered in the case of the second scratch even if the length is a length that would not result in a judgement of "defective" in the case of the first scratch.

Figure 13:
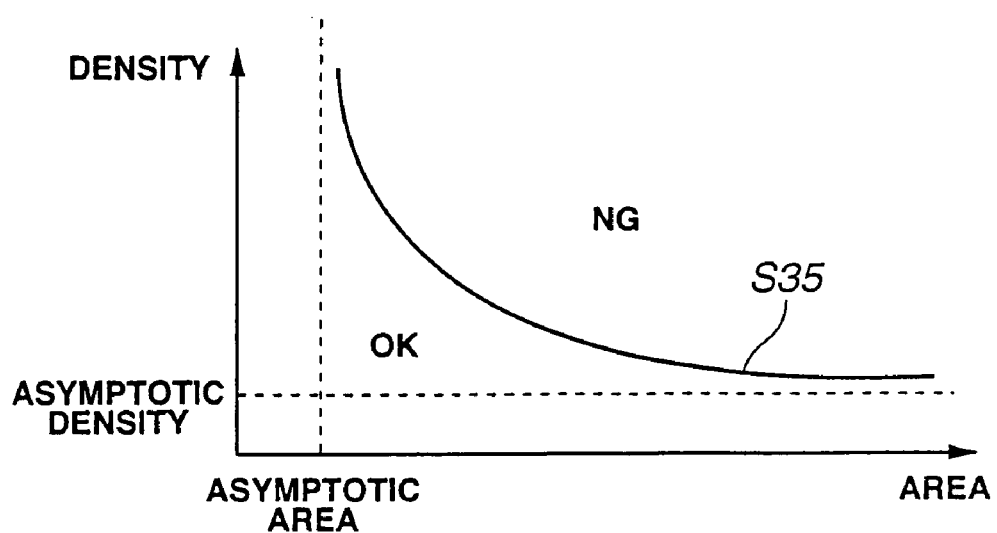
FIG. 13 is a schematic diagram which is used to illustrate the staining reproduction method of the present invention.

Furthermore, the system is devised so that in the judgement processing step A14 shown in FIG. 4, the judgement computer 21 judges the types of staining in accordance with the aggregate state (characterizing quantities) of the scattering points described above with reference to FIG. 12, and varies the judgement criteria (area-density judgement curve S35) describe above with reference to FIG. 13 in accordance with the type of staining in question.

FIG. 15(A) is a diagram which illustrates the detection method used by the judgement computer 21 to detect scratches and staining; furthermore, FIG. 15(B) is a diagram which shows the judgement criteria used to judge defective wafers. Here, the length, depth, area and density of scratches and staining are used as characterizing quantities for the purpose of classifying the scratches and staining. However, characterizing quantities that can be used for scratches include length, density, width, linearity, curvature, position and the like, and characterizing quantities that can be used for staining include area, depth/density, distribution, shape, position and the like. The judgement computer may use these characterizing quantities as required.

A judgement regarding "defective" status is performed by the judgement computer 21 on the basis of scratches and staining on the surface of the silicon wafer, and the results are output using a printer or the like.

Operation

In the silicon wafer surface inspection device of the present invention (judgement computer 21) which has the functions and construction described above, scratches and staining are extracted as information regarding aggregation and cluster of scattering points (LPD) 31, and the types and degree of these extracted scratches and staining are classified according to the characterizing quantities of these scratches and staining. In most cases, the types and degree of scratches and staining vary according to the cause of generation of such scratches and staining; depending on this cause of generation, there may be instances in which even small scratches or areas of staining are cause for a judgement of "defective". Accordingly, since the judgement computer 21 renders a judgement of "defective" using "defective" judgement criteria that differ according to the types and degree of classified scratches and staining (aggregation and cluster), the problem of good wafers being judged as "defective", or of wafers that should be judged as "defective" being judged as "good", can be avoided, so that an accurate judgement can be made.

Furthermore, since aggregation and cluster of scattering points 31 are recognized as scratches and staining by the judgement computer 21, there is no need for workers to judge scratches and staining. Moreover, the judgement results of the judgement computer 21 can be confirmed via an LAN in a computer 14 (FIG. 1) installed outside the clean room, so that there is no need for workers to enter the clean room when performing various types of confirmation work; accordingly, the working efficiency can be improved.

Other Embodiments

Furthermore, in the embodiment described above, a case was described in which pyramid processing and an interval analysis method using a rotational projection method were used in combination as the method used to detect scratches on the silicon wafer surface. However, the present invention is not limited to such a method; it would also be possible to use one method or the other.

Furthermore, in the embodiment described above, a case was described in which "defective" status was judged on the basis of the length of linear scratches, and "defective" status of staining was judged on the basis of the area and density of the staining. However, the present invention is not limited to such a method; it would also be possible to judge the "defective" status of linear scratches on the basis of the width (thickness) of such scratches, and to use characterizing quantities of scratches and staining such as area, height, linearity, curvature, position, number of scattering points 31 constituting the defects (scratches or staining), density, size distribution and the like in the determination of "defective" status.

Effects of the Invention

As was described above, the silicon wafer surface inspection device of the present invention makes it possible to detect scratches and staining of a length and size that are cause for a judgement of "defective", so that the inspection efficiency can be improved.

Furthermore, the silicon wafer surface inspection device of the present invention makes it possible to use "defective" judgement criteria such as length and size in accordance with the types of scratches and staining, so that the precision of judgements as "defective" can be further improved.

Next, the wafer surface information processing device will be described.

Construction of the Apparatus

In addition to detection of the abovementioned scratches and staining (generation of wafer surface information), and judgement processing used to judge defective wafers, the surface inspection system 10 which has the abovementioned judgement computer 21 also has the function of specifying the processes in which scratches and staining are generated.

Figure 16:
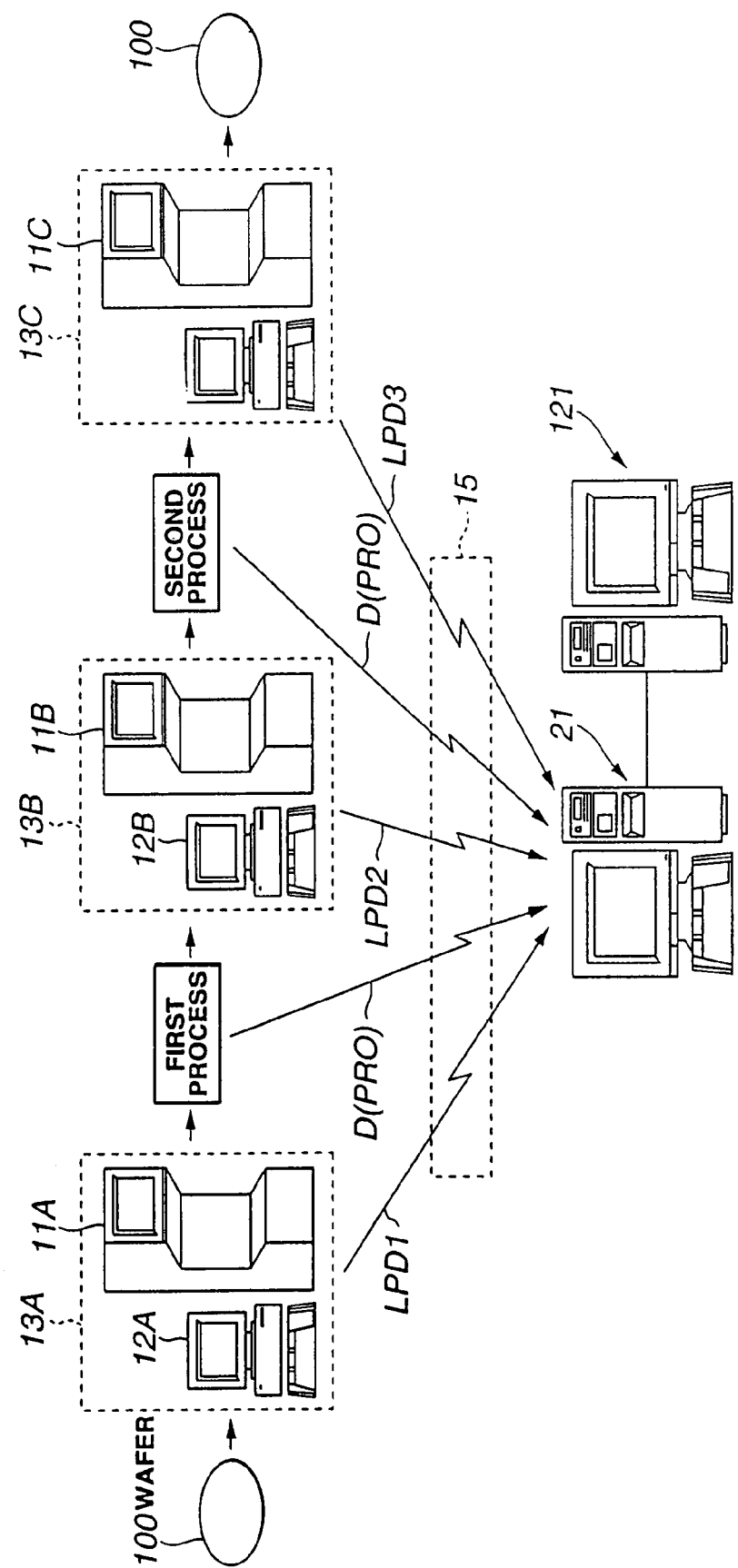
FIG. 16 is a block diagram which shows the overall construction of a system using the surface information processing device of the present invention.

Specifically, FIG. 16, in which parts that correspond to parts in FIG. 1 are labeled with the same symbols, is a block diagram showing an example of construction used in a case where respective extraction parts 13 (13A, 13B and 13C) that have laser scattering detectors 11 (wafer surface inspection devices) 11 (11A, 11B and 11C) are disposed before and after respective manufacturing processes of the wafer 100 (e.g., a first process which is a surface polishing process and a second process which is a cleaning process).

In this FIG. 16, the LPD maps LPD1, LPD2 and LPD3 that are detected by the respective laser scattering detectors 11A, 11B and 11C are respectively stored on the hard disk of the judgement computer 21 in correspondence with the respective sets of process information. Specifically, wafer IDs, slot numbers and the like for the respective LPD maps are attached to the respective LPD maps LPD1, LPD2 and LPD3 that are output for each wafer from the respective laser scattering detectors 11A, 11B and 11C, and the judgement computer 21 stores such wafer specifying information as well as information specifying the laser scattering detector 11A, 11B or 11C that is the output source of each LPD map (respective IDs of the laser scattering detectors 11A, 11B and 11C), along with the LPD maps.

The information that specifies the laser scattering detectors that are the output sources of the LPD maps stored in the judgement computer 21 is accumulated in the judgement computer in a time sequence with this information being caused to correspond to the wafer IDs, slot numbers and the like of the wafers that correspond to this information. Accordingly, the judgement computer 21 can confirm the process history and final process at the current point in time of a certain wafer by means of the ID of the laser scattering detector accumulated for this wafer (such accumulated information is called process history information).

Accordingly, for example, process history information for the LPD map LPD1 that has been output from the laser scattering detector 11A disposed before the first process is in a state in which no information has been accumulated; from this, the judgement computer 21 can confirm that the LPD map LPD1 is an LPD map for a wafer that has not yet entered the first process. Furthermore, the process history information corresponding to the LPD map LPD2 that has been output from the laser scattering detector 11B disposed before the second process is in a state in which only information indicating the first laser scattering detector 11A has been accumulated; from this, the judgement computer 21 can confirm that the LPD map LPD2 is an LPD map for a wafer that has just completed the first process, i.e., that has not yet entered the second process.

Incidentally, instead of accumulating and utilizing the IDs of the respective laser scattering detectors 11, it would also be possible to supply the wafer IDs and slot numbers of the wafers treated in the respective processes as process information D (PRO) to the judgement computer 21 via a network 15 as shown in FIG. 16. In this case, the judgement computer 21 can use the wafer IDs supplied from the respective processes to confirm which processes have been completed by the wafers specified by these wafer IDs, and to recognize the process history of these wafers.

Thus, the respective LPD maps supplied from the respective laser scattering detectors 11 are accumulated in the judgement computer 21 with these LPD maps being caused to correspond to the process history information of the respective wafers. These accumulated LPD maps are used in the detection of scratches and staining in the processing steps described above with respect to FIG. 4.

Information concerning scratches and staining detected in the processing routine shown in FIG. 4 (wafer surface information) is produced as the image information shown in FIGS. 14 and 10(C) and numerical information such as the position, size, depth and the like of such scratches and staining in the judgement computer 21, and the system is devised so that the judgement computer 21 superposes these sets of surface information for wafers that have the same process history. The results of this superposition are supplied to the supporting device 121, and are utilized to specify the processes in which the scratches and staining are generated.

Figure 17:
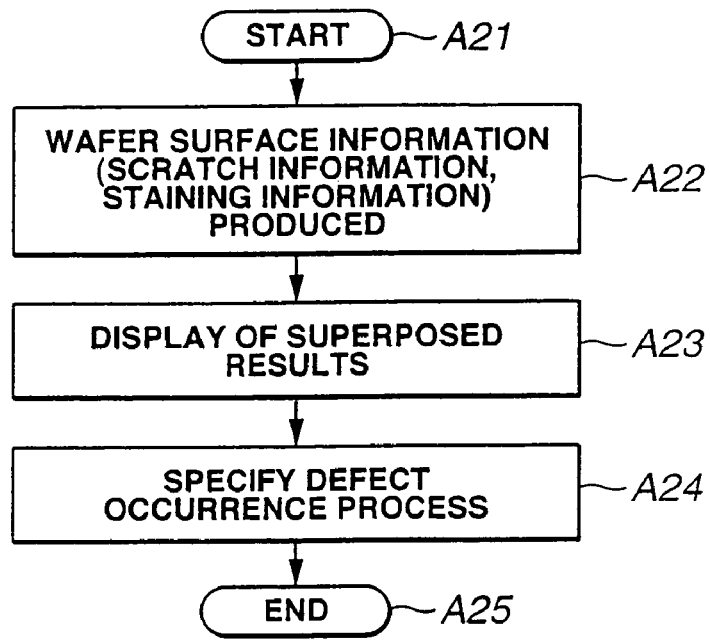
FIG. 17 is a flow chart which shows the processing routine used to specify the process in which defects are generated in the present invention.

Specifically, FIG. 17 shows the processing routine specifying defective processes that is performed by the judgement computer 21 and supporting device 121. When the judgement computer 21 enters this processing routine from step A21, wafer surface information that has already been produced by the scratch and staining detection processing described above with reference to FIG. 4 is superposed for wafers that have the same process history in step A22.

Figure 18:
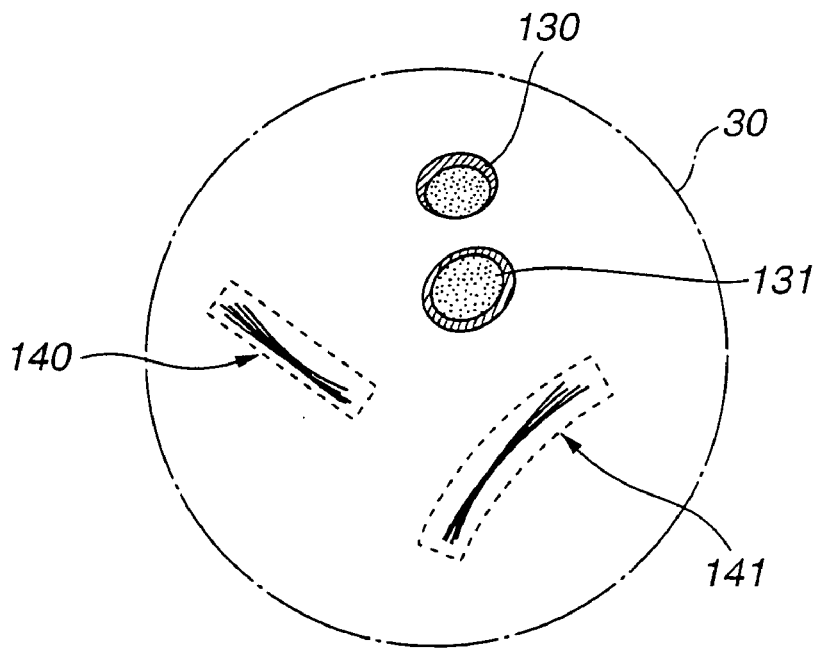
FIG. 18 is a schematic diagram which shows the results of superposition of surface information in the present invention.

As a result, as is shown in FIG. 18, scratches that are generated in the same position are superposed in the same position, so that if the frequency of occurrence of scratch information or staining information in a certain range (areas 140, 141, 130 and 131 in FIG. 18) increases, this means that scratches and staining that are sufficient to cause the wafer to be judged "defective" are constantly being generated in some of the process histories of the respective wafers in which the surface information in this case is superposed (the process histories of the respective wafers in which the surface information is superposed in this case are the same).

Accordingly, after displaying the superposed results as an image on the monitor in step A23, the judgement computer 21 supplies this superposed data to the supporting device 121, and the defective process specifying processing of step A24 is performed in the supporting device 121.

Figure 19:
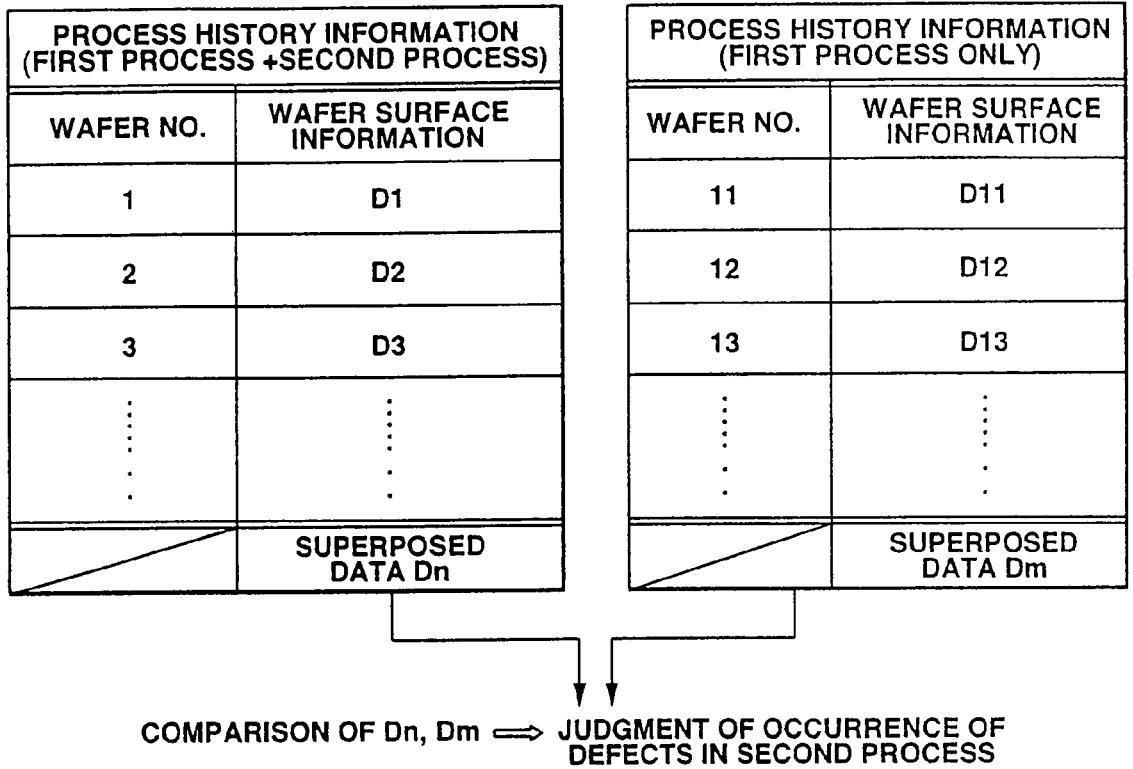
FIG. 19 is a schematic diagram which shows the surface information and process information used in the present invention.

In this specifying processing, the supporting device 121 compares superposed data in which the final process differs by one process (e.g., the superposed data Dn and Dm shown in FIG. 19) among the respective sets of superposed data in which surface information corresponding to the respective sets of process history information is superposed. For example, as is shown in FIG. 19, the superposed data Dn formed by superposing the surface information D1, D2, . . . in which the process history consists of only the first process (i.e., data for which the final process is the first process) and the superposed data Dm formed by superposing the surface information D11, D12, . . . in which the process history consists of the first process and second process (i.e., data for which the final process is the second process) differ in terms of whether or not the second process is included in the data. Accordingly, the supporting device 121 compares these sets of superposed data, and in cases where scratches and staining with a high frequency of occurrence are absent from one set of superposed data but present in the other set of superposed data, the supporting device 121 can ascertain that the cause of the generation of these scratches and staining is in the second process.

The supporting device 121 stores such judgement results and the abovementioned superposed results on a memory medium such as a hard disk or the like, and outputs these results to a monitor or printer, after which this processing routine is ended in step A25.

Incidentally, instead of using data for different wafers as the superposed data used for judgement as described above, it would also be possible to store superposed data for the same wafer each time that the process history is added, and to compare this stored superposed data for the same wafer.

Figure 22:
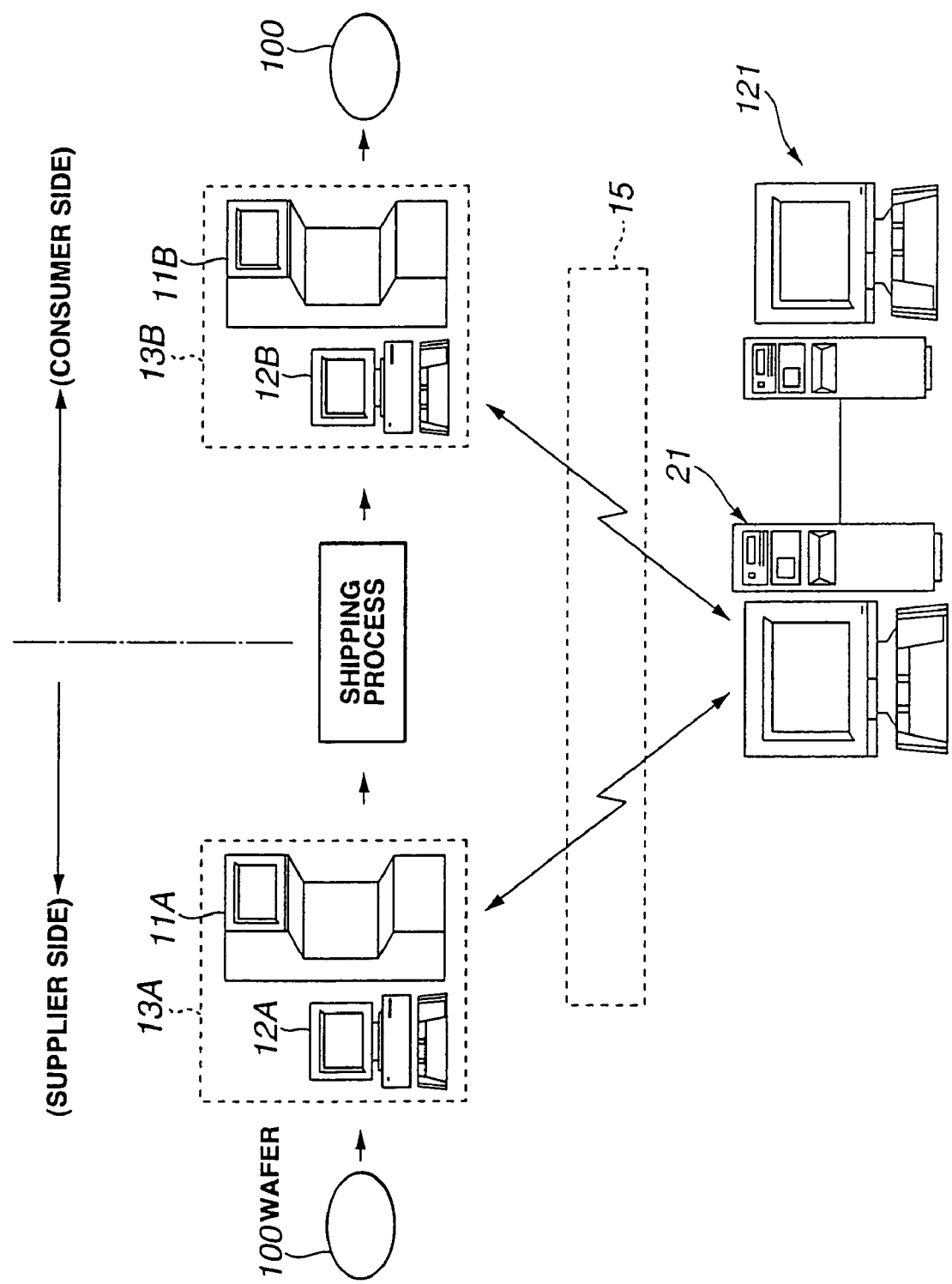
FIG. 22 is a block diagram which shows an embodiment in which surface inspection devices (laser scattering detection devices) are installed on the side of the supplier and the side of the consumer in the present invention.

Next, a case will be described in which the process described above with reference to FIG. 16 is a shipping process in which wafers are shipped from a wafer supplier to a consumer. In FIG. 22, in which parts that correspond to parts shown in FIG. 16 are labeled with the same symbols, the system is devised so that laser scattering detectors 11A and 11B that constitute wafer surface inspection devices are respectively disposed on the side of the wafer supplier and the side of the consumer at both ends of the shipping process, and LPD maps produced as a result of wafer surface inspection in theses laser scattering detectors 11A and 11B are received by the judgement computer 21. Here, it is assumed that the judgement computer 21 and supporting device 121 are in the possession of the wafer supplier or some other service worker.

The wafer supplier inspects the surfaces of manufactured wafers 100 by means of the laser scattering detector 11A. These inspection results are produced as an LPD map, and are supplied to the judgement computer 21. On the basis of the LPD map supplied from the wafer supplier, the judgement computer 21 performs the detection and "defective" judgement of scratches and staining suing the inspection and judgement methods described above with reference to FIGS. 1 through 15. Then, only wafers that are judged to be "good" among the wafers thus inspected are shipped to the consumer by (for example) a shipper.

The wafer consumer uses the laser scattering detector 11B disposed on the side of the consumer to inspect the inspected wafers that have been shipped from the supplier. These inspection results are produced as an LPD map and are supplied to the judgement computer 21.

The judgement computer 21 superposes the scratch information and staining information produced on the basis of the LPD map supplied from the supplier for a plurality of wafers, and superposes the scratch information and staining information produced on the basis of the LPD map supplied from the consumer for a plurality of wafers. The superposed results are supplied to the supporting device 121. Then, these sets of superposed data are compared, and in cases where results are obtained in which scratches and staining with a high frequency of occurrence are present in the superposed data on the side of the consumer but not in the superposed data on the side of the supplier, the supporting device 121 can judge that the cause of the occurrence of such scratches and staining is in the shipping process. Incidentally, the superposed data that is compared by the supporting device 121 may be either superposed data for the same wafer or superposed data for different wafers.

Information concerning the process in which defective products are generated (wafer surface information, superposed data, information specifying the process in which defects are generated or the like), as ascertained by the supporting device 121, may be referred to by either the supplier (judgement computer 21 or control computer 12A) or the consumer (control computer 12B) via the network (including the network 15), so that mutual understanding of the intentions of the supplier and consumer regarding processes (the shipping process or the like) is facilitated on the basis of this information, and the consumer can easily transmit his own requirements to the supplier. As a result, the supplier can plan improvements that make it possible to supply wafers of a quality that accurately meets the requirements of the consumer.

Operation

In the silicon wafer surface information processing device of the present invention which has the abovementioned functions and construction (i.e., the judgement computer 21 and supporting device 121), scratches and staining are produced as image information and information consisting of various numerical values or the like on the basis of an LPD map supplied from a laser scattering detector 11; afterward, the surface information thus produced is superposed for a plurality of wafers. In this case, if there is a tendency for large quantities of scratches and staining to be generated in a certain position on the wafer surface, the amount of superposition of the same scratches and staining will be increased in this position as a result of superposition.

Accordingly, by viewing the superposed results, it is possible to judge whether the scratches and staining detected for individual wafers have been generated by chance in these wafers alone, or whether such scratches and staining are constantly generated.

The process in which scratches and staining are generated can be specified by means of the process history information that is caused to correspond to the surface information for the respective wafers. Using this process history information, the supporting device 121 can specify the process in which scratches and staining are generated. Accordingly, the operator can easily find processes in which defects are generated merely by viewing the results of this specification. Then, by inspecting and improving the defect-generating process thus found, the operator can quickly eliminate the continuous generation of defective products, and can thus improve the working process.

In particular, the setting of plans for improving the shipping process is facilitated, since the generation of defects in the process of shipping from the wafer supplier to the consumer can be detected by the supporting device 121. Information regarding the occurrence of such defects can be referred to by either the wafer supplier or the consumer; the supplier and consumer can refer to such information and achieve a mutual understanding of intentions, so that the causes of defects can be specified, and improvements in the shipping process can be planned.

Other Embodiments

Furthermore, in the abovementioned embodiment, as was described with reference to FIG. 17, a case was described in which scratches and staining detected on the basis of an LPD map were produced as image information and various types of numerical information in the judgement computer 21, and superposed data was obtained by superposing the information (surface information) thus produced. However, the present invention is not limited to such a system; it would also be possible to devise the system so that an LPD map supplied from the laser scattering detector 11 is superposed as wafer surface information by the judgement computer 21 and supporting device 121. The processing routine used in this case is shown in FIG. 20.

Figure 20:
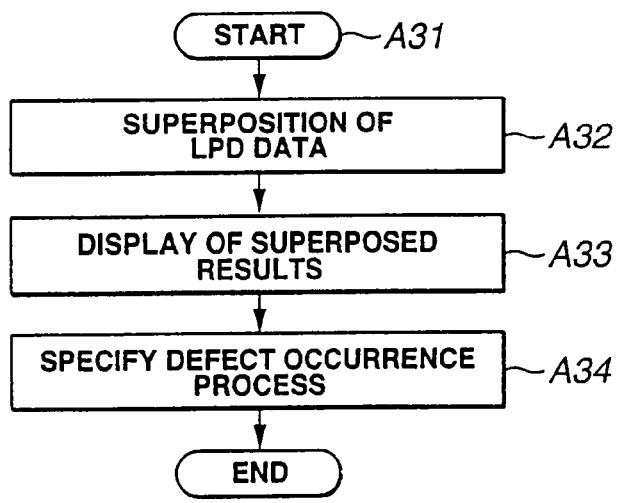
FIG. 20 is a flow chart which shows another embodiment of the processing routine used to specify the process in which defects are generated in the present invention.

Specifically, FIG. 20 shows another embodiment of the specifying processing routine for specifying "defective" processes that is performed by the judgement computer 21 and supporting device 121. When the judgement computer 21 enters this processing routine from step A31, an LPD map that is supplied from the laser scattering detector 11 described above with reference to FIG. 3 is superposed for wafers with the same process information in step A32.

Figure 21:
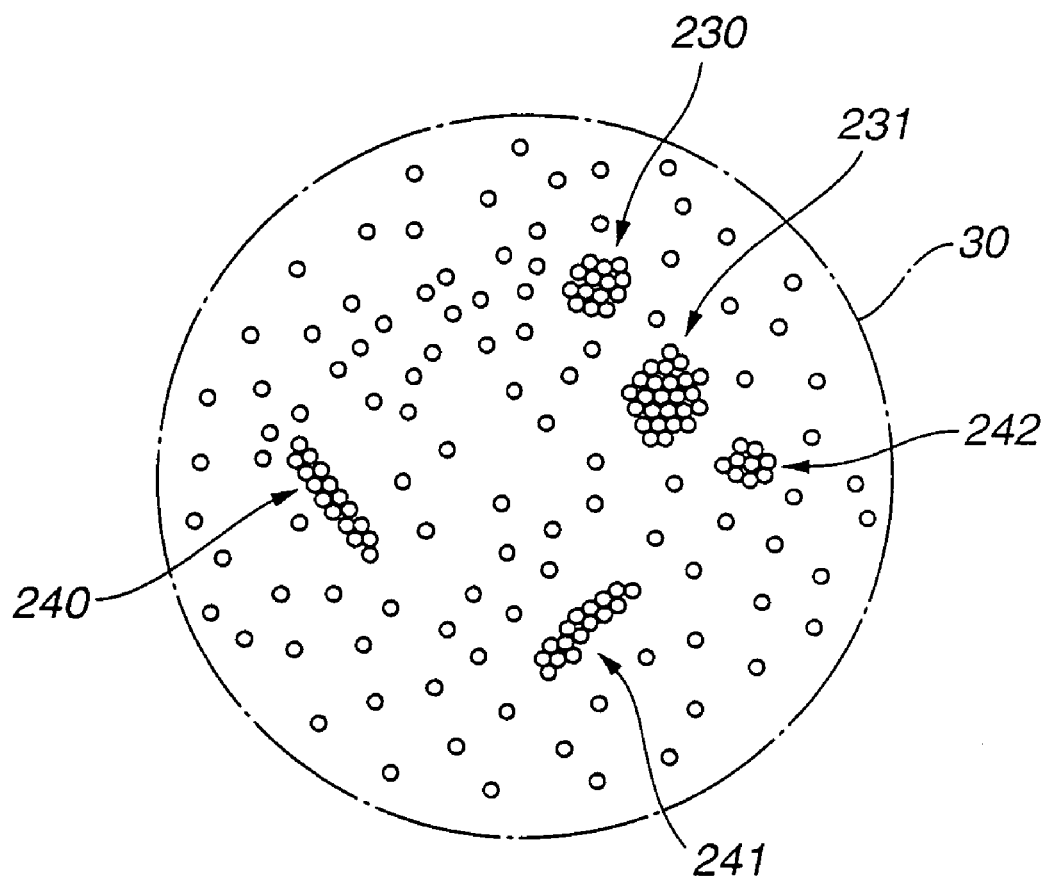
FIG. 21 is a schematic diagram which shows the results of superposition of the LPD map in the present invention.

As a result, as is shown in FIG. 21, LPDs generated in the same position are superposed in the same position, and when the frequency of occurrence of LPDs in a certain range (areas 240, 241, 230 and 231 in FIG. 21) increases, this means that scratches and staining constituting cause to judge the wafer as "defective" are constantly being generated in some of the process histories of the respective wafers for which the LPD maps are superposed in this case. Incidentally, the method described above with reference to FIGS. 1 through 15 is used as the detection method that detects scratches and staining on the basis of the LPDs that are superposed in this case.

After displaying the superposed results and detection results in step A33, the judgement computer supplies this superposed data to the supporting device 121, and the "defective" process specifying processing of step A34 is performed by this supporting device 121. This "defective"

process specifying processing is the same as that of the processing step A24 described above with reference to FIG. 17.

Thus, the judgement computer 21 and supporting device 121 can specify processes that are the cause of scratches and staining by directly superposing the LPD maps. In cases where LPD maps are thus directly superposed, defects in which fine LPDs that would not be viewed as scratches or staining in individual wafers are constantly generated in the same position (area 242 shown in FIG. 21) can also be detected in addition to defects caused by external factors such as scratches and staining.

Furthermore, in the embodiment described above, a case was described in which the processes through which the wafer had passed were recorded as process history information. However, the present invention is not limited to such a system; it would also be possible to use various other methods such as recording only the final process at the current point in time or the like.

Furthermore, in the embodiment described above, a case was described in which wafer surface information was superposed in the judgement computer 21, and the defect-generating process was specified by supplying the superposed data obtained by this superposition. However, the present invention is not limited to such a system; it would also be possible to devise the system so that scratch information and staining information (wafer surface information) detected and produced in the judgement computer 21 are supplied to the supporting device 121, and this surface information is superposed in the supporting device 121.

Furthermore, in the embodiment described above, a system which had one judgement computer 21 and one supporting device 121 was described. However, the present invention is not limited to such a system; it would also be possible to devise the system so that respective sets of surface information and superposed data are shared by a plurality of judgement computers 21 and supporting devices 121.

Furthermore, in the embodiment described above, a system was described in which the detection of scratches and staining and the specification of the processes in which such scratches and staining were generated was performed. However, the present invention is not limited to such a system; it would also be possible (for example) to devise the system so that the quality required by the consumer in wafers is retained in the judgement computer 21 or supporting device 121, wafers that are judged to be of a quality inferior to this required quality are ascertained, and the process in which the defects occurring in these wafers are generated is specified. In this case, the term "quality" refers to the quality judged on the basis of the shape, depth and the like of the scratches and staining in the judgement processing described above with reference to FIG. 4.

Furthermore, in the abovementioned embodiment, a case was described in which laser scattering detectors 11A, 11B and 11C were disposed between a plurality of processes, and processes in which defects were generated were specified on the basis of LPD maps obtained from the plurality of laser scattering detectors 11A, 11B and 11C (i.e., LPD maps detected between the respective processes). However, the present invention is not limited to such a system; for example, it would also be possible to devise the system so that defect-generating processes are judged only on the basis of an LPD map obtained from a laser scattering detector 11C installed after the overall process or after the final process among specified process units.

In this case, trends of the contents of defects (positions of scratches and staining, radius of curved scratches and the like) generated in the respective processes are stored beforehand in the judgement computer 21 or supporting device 121, the LPD map detected after the final process is superposed in the same manner as in the case described above with reference to FIG. 17 or FIG. 19, and scratch information and staining information (wafer surface information) are detected on the basis of the superposed results. Then, on the basis of wafer surface information that agrees with the pre-stored trends in the contents of defects (among the wafer surface information thus detected), processes that show such trends in defect generation are specified. If this is done, then processes in which defects are generated can be specified without installed laser scattering detectors between the respective processes. Incidentally, the items described above as characterizing quantities of scratches and staining (characterizing quantities for scratches include length, density, width, linearity, curvature, position and the like, and characterizing quantities for staining include area, depth/density, distribution, shape, position and the like) can be used as information that expresses trends in defect generation for each process.

Furthermore, in the embodiment described above, a case was described in which superposed data was produced in the judgement computer 21, and the generation of defects in the shipping process between the supplier and the consumer was judged on the basis of this superposed data in the supporting device 121. However, the present invention is not limited to such a system; it would also be possible to devise the system so that scratches and staining are detected on the basis of an LPD map obtained from the laser scattering detector 11B in the control computer 12B on the consumer side, good products or defective products are judged on the basis of this scratch information and staining information, and information (wafer ID, slot number, scratch and staining information and the like) concerning wafers judged to be defective as a result of this judgement is transmitted to the judgement computer 21 or control computer 12A on the side of the supplier, so that this wafer information can be compared in the control computer 12A or judgement computer 21 with scratch and staining information for this wafer or other wafers that has been stored beforehand, thus making it possible to judge whether or not the cause of the generation of defects is in the shipping process.

Furthermore, in the embodiment described above, a case was described in which LPD maps supplied from the laser scattering detectors 11A, 11B and 11C were converted into scratch information and staining information consisting of image information or numerical information, after which this information was superposed in the judgement computer 21. However, the present invention is not limited to such a system; it would also be possible to devise the system so that LPD maps supplied from the laser scattering detectors 11A, 11B and 11C are directly superposed in the judgement computer 21 without being converted into scratch information or staining information.

Furthermore, in the embodiment described above, a case was described in which the processes through which each wafer had passed were recorded as process history information. However, the present invention is not limited to such a system; it would also be possible to use various other methods such as recording only the final process at the current point in time or the like.

Furthermore, in the embodiment described above, a case was described in which laser scattering detectors 11A and 11B were respectively disposed before and after the shipping process, and the presence or absence of generation of defects was judged on the basis of LPD maps obtained from the plurality of laser scattering detectors 11A and 11B (i.e., a plurality of LPD maps detected before and after the shipping process). However, the present invention is not limited to such a system; it would also be possible to devise the system so that the generation of defects is judged only on the basis of an LPD map obtained from the laser scattering detector 11B disposed following the shipping process.

In this case, trends in the contents of defects generated in the shipping process (positions of scratches and staining, radius of curved scratches and the like) are stored beforehand in the supporting device 121, the LPD maps detected following the shipping process are superposed in the same manner as in the case described above with reference to FIG. 17, and scratch information and staining information (wafer surface information) are detected on the basis of the superposed results. Then, wafer surface information that agrees with the pre-stored trends in the contents of defects (among the wafer surface information thus detected) is judged to consist of defects that are generated by the shipping process, and this is indicated visually on a monitor or the like. If this is done, the generation of defects can be judged using only information obtained on the side of the consumer, and judgements comparable to those made in cases where the superposed data of LPD maps respective obtained from the side of the supplier and the side of the consumer are compared can be achieved. Incidentally, a method in which LPD maps before and after various types of shipping processes are detected in test mode, and the contents of these shipping processes are associated with trends in the generation of defects caused by these shipping processes by comparing these LPD maps, can be used as the method that is used to pre-store the trends in the generation of defects in the shipping process.

In this case, furthermore, the items described above as characterizing quantities of scratches and staining (characterizing quantities for scratches include length, density, width, linearity, curvature, position and the like, and characterizing quantities for staining include area, depth/density, distribution, shape, position and the like) can be used as information that expresses trends in defect generation in the shipping process. Furthermore, in this case as well, the process that is the object of judgement of defect generation is not limited to a shipping process; similar judgements can be made for various other types of processes.

Figure 23:
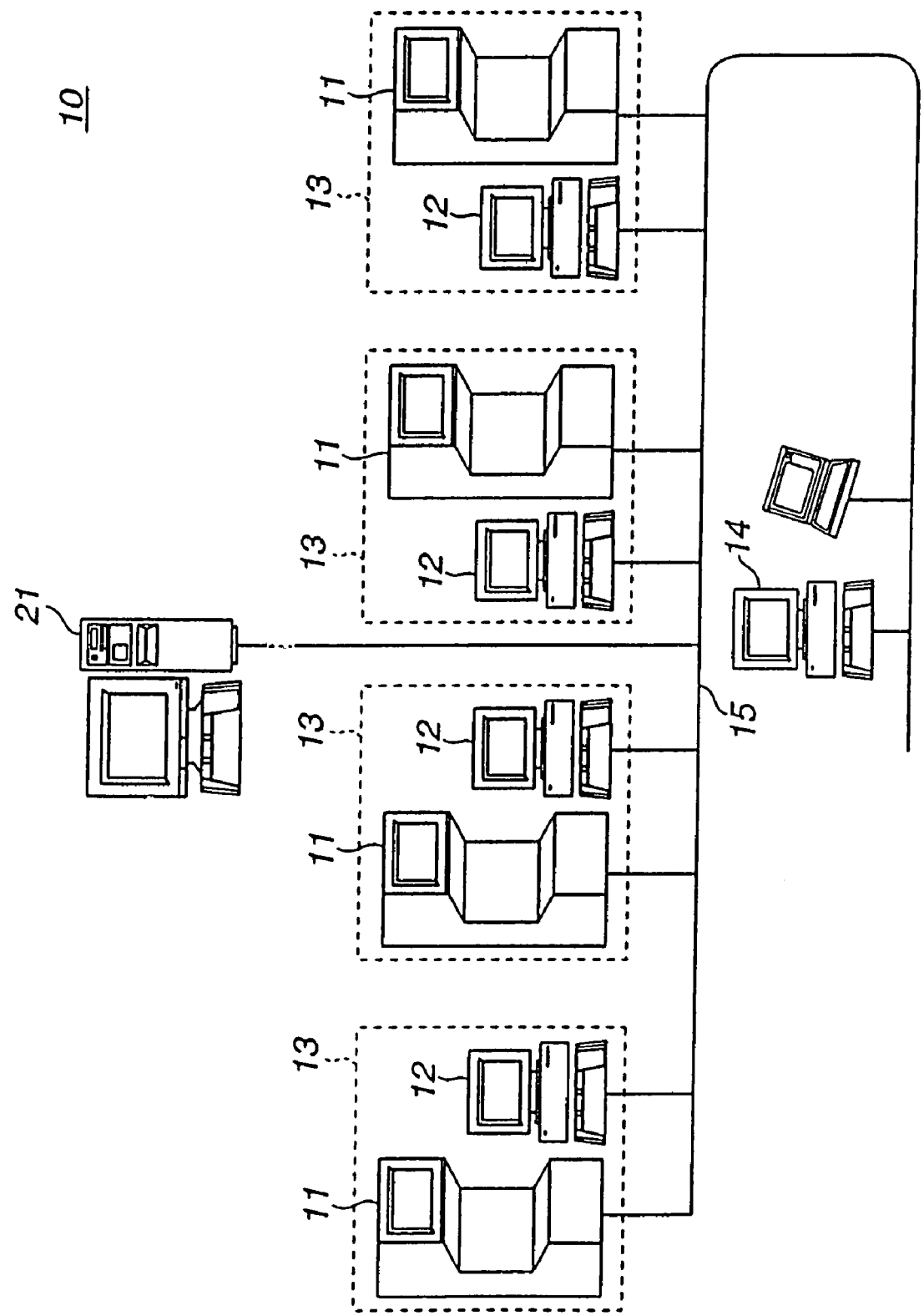
FIG. 23 is a schematic diagram which shows the overall construction of a silicon wafer inspection system that differs from that shown in FIG. 1.

Furthermore, it would also be possible to devise the system so that defects that are constantly generated are detected by superposing wafer surface information that expresses scratches and staining by means of the judgement computer 21, without connecting a supporting device 121 to the judgement computer 21 (as shown in FIGS. 23, 24 and 25).

Effects of the Invention

As was described above, the silicon wafer surface information processing device of the present invention makes it possible to detect scratches and staining that are constantly generated by superposing wafer surface information; furthermore, this device also makes it possible to detect the process in which the defects are generated (e.g., generation of defects in the shipping process). Moreover, since information concerning the process in which defects are generated (e.g., the shipping process) is shared by both the wafer supplier and consumer, specification of the process in which defects are generated and the improvement of this process can easily be accomplished by both the supplier and the consumer.

INDUSTRIAL APPLICABILITY

The present invention can be used in treatment processes in wafer manufacture, or in shipping processes.

The invention claimed is:

1. A wafer surface inspection device which detects scratches on a plurality of wafer surfaces on the basis of two-dimensional defect distribution information (an LPD map) for each wafer surface of the plurality of wafer surfaces supplied from a particle counter, and judges the acceptability of the wafer surface whereby the wafer surface inspection device prepares a report, comprising:

input means for inputting the LPD map supplied from the particle counter;

memory means for accumulating the LPD map for each of the plurality of wafers; and information processing means for the detection of the scratches on the wafer surface by detecting the cluster of LPD in the LPD maps accumulated in the memory means from said plurality of wafers and preparing a wafer surface information thereon;

and judgment means for judging the existence of defects on a single wafer surface based on the wafer surface information prepared by the information processing means, whereby the report prepared by said wafer surface inspection device based on the judging concerning the acceptability of the wafer surface is provided to a user.

2. The wafer surface inspection device according to claim 1, characterized in that the information processing means detects defects by detecting aggregation of linearly clustered LPD by means of two-dimensional half-conversion processing for each partial area of the LPD map.

3. The wafer surface inspection device according to claim 1, characterized in that the information processing means further detects indefinite-form aggregation of LPD as defects in distinction from surrounding areas by smoothing at least a portion of the LPD map by means of a space filter, and binarizing the result of smoothing with a specified threshold value.

4. A judgment device for judging the acceptability of an individual wafer surface that has scratches and staining on its surface and preparing a report for a user on the basis of information concerning scratches and staining supplied from a wafer surface inspection device that detects the scratches and staining on the wafer surface on the basis of an LPD map, comprising:

input means for inputting the information concerning scratches and staining on a plurality of wafers that are supplied from the wafer surface inspection device;

memory means capable of accumulating the information concerning scratches and staining for each of the plurality of wafers; and information processing means for detecting a type of scratches on an individual wafer surface from characteristic quantities relating to the scratches in the accumulated information stored in the memory means, said information processing means detecting a type of the scratches, detecting a degree of the staining on an individual wafer surface from characteristic quantities relating to staining in information stored in the memory means, and performing a judgment on the basis of criteria corresponding to the type of the detected scratches and/or on the basis of criteria corresponding to the degree of the detected staining, and thereby identifying acceptable individual wafers based on the judgment and preparing said report for the user based on said judgment.

5. The judgment device according to claim 4, characterized in that the characteristic quantities relating to the scratches or staining are a depth and size of the scratches or staining.

6. The judgment device according to claim 4, characterized in that the characteristic quantities relating to the scratches constitute one or more items selected from a group consisting of a length, density, width, linearity, curvature and position of the scratches.

7. The judgment device according to claim 4, characterized in that the characteristic quantities relating to the staining constitute one or more items selected from a group consisting of an area, depth/density, distribution, shape and position of the staining.

8. A wafer surface information processing device for determining the acceptability of a wafer surface and preparing a report for a user thereon, comprising:
input means for inputting wafer surface information comprising scratch information and staining information related to the wafer surfaces of a plurality of wafers that is supplied from a wafer surface inspection device;
memory means for accumulating the wafer surface information for each of the plurality of wafers;
superposing means for forming superposed surface information by superposing wafer surface information accumulated in the memory means;
display means for displaying the superposed surface information formed by the superposing means; and
information processing means for detecting scratches and staining on the plurality of wafer surfaces that occur at a high frequency by detecting the cluster of point defects (LPD) in the superposed surface information from said plurality of wafers, said information processing means for preparing a report for a user related to the detected scratches and stains from the plurality of wafer surfaces, said report being usable by the user for determining the acceptability of an individual wafer surface.

9. The wafer surface information processing device according to claim 8, characterized in that the wafer surface information for each of the wafers and the superposed surface information are respectively displayed as images on the wafers.

10. The wafer surface information processing device according to claim 8, characterized in that the device is devised so that a judgment of the process in which scratches or staining have been generated can be supported by pre-recording the trend of particulars of generated defects for each process through which each wafer passes, and by outputting wafer surface information that matches this trend in particulars of generated defects.

11. The wafer surface information processing device according to claim 8, characterized in that the device is devised so that the judgment of the process in which scratches or staining have been generated can be supported by accumulating the wafer surface information in correspondence with wafer history information recording the processes through which each wafer has passed, and by outputting wafer surface information corresponding to the wafer history information.

12. The wafer surface information processing device of claim 11, further including a supporting device for supporting the judgment of causes of generation of scratches and staining on wafer surfaces in wafer manufacturing processes, comprising input means, memory means, processing means and output means, wherein the output wafer surface information is extracted via the input means from the wafer surfaces, the extracted output wafer surface information from a plurality of wafer surfaces is accumulated by the memory means, the processes in which scratches and staining are frequently generated are calculated by the processing means on the basis of the accumulated and a result concerning said process is output from the output means.

13. The wafer surface information processing device of claim 11, further including a supporting device for supporting the judgment of a monetary amount to be covered by insurance during the conveyance of wafers, comprising input means, memory means, processing means and output means, wherein the output wafer surface information is extracted via the input means, the extracted output wafer surface information is accumulated by the memory means, the monetary amount to be covered by insurance is calculated by the processing means on the basis of the accumulated output wafer surface information, and a result concerning said monetary amount is output from the output means.

14. A wafer surface information processing device for use in determining the acceptability of a wafer surface and preparing a report thereon for a user comprising:
input means for inputting wafer surface information comprising scratch information and staining information compiled from a plurality of wafer surfaces for each individual wafer that is supplied from two wafer surface inspection devices;
memory means for accumulating the wafer surface information for each of the plurality of wafers;
superposing means for forming superposed surface information by superposing said wafer surface information accumulated in the memory means;
display means for displaying respective sets of wafer surface information or respective sets of superposed surface information of the two wafer surface inspection devices in contrast with each other; and
information processing means for processing information related to the wafer surface information accumulated in the memory means, and for comparing the respective sets of superposed wafer surface information whereby the information processing means forms a judgment concerning the acceptability of the wafer surface and for preparing said report for the user based on said judgment.

15. The wafer surface information processing device according to claim 14, wherein the wafer surface information and the superposed surface information for each wafer are respectively displayed as images on the wafer.

16. The wafer surface information processing device according to claim 14, characterized in that the two wafer surface inspection devices are respectively disposed at a starting point and an end point of a certain wafer processing process.

17. The wafer surface information processing device according to claim 14, characterized in that the two wafer surface inspection devices are respectively disposed on the side of a wafer supplier and on the side of a wafer consumer.

18. The wafer surface information processing device according to claim 17, characterized in that a transmitting device which transmits data for wafers judged to be defective by the wafer consumer is disposed in the wafer surface inspection device located on the side of the wafer consumer.

19. The wafer surface information processing device according to claim 17, characterized in that a receiving device which receives data for wafers transmitted by the wafer consumer as a result of the wafers being judged to be defective is disposed in the wafer surface inspection device located on the side of the wafer supplier.

20. A wafer surface information processing device for determining the acceptability of a wafer surface from a plurality of wafer surfaces and preparing a report for a user comprising:

input means for inputting wafer surface information from each wafer surface of the plurality of wafer surfaces comprising scratch information and staining information for a wafer surface for each wafer that is supplied from a wafer surface inspection device;

memory means for accumulating the wafer surface information for each of a plurality of wafers;

superposing means for forming superposed surface information by superposing wafer surface information accumulated in the memory means;

recording means for recording in the memory means a trend of particulars of generated defects in the process from the plurality of wafer surfaces; and output means for outputting the wafer surface information or the superposed surface information that matches the trend of particulars of generated defects, wherein the device judges from the superposed surface information whether or not scratches and staining are generated in the process, and provides information for determining the acceptability of the wafer surface and prepares said report for the user thereon.

\* \* \* \* \*

UNITED STATES PATENT AND TRADEMARK OFFICE
CERTIFICATE OF CORRECTION

PATENT NO. : 7,383,156 B2  Page 1 of 1
APPLICATION NO. : 10/363746
DATED : June 3, 2008
INVENTOR(S) : Matsusita et al.

It is certified that error appears in the above-identified patent and that said Letters Patent is hereby corrected as shown below:

On Title page Item [73]
Please delete Assignee "SUMCO TECHXIV KABUSHIKI KAISHA" and insert --SUMCO TECHXIV CORPORATION--.

Signed and Sealed this

Twelfth Day of August, 2008

JON W. DUDAS
*Director of the United States Patent and Trademark Office*